US012710433B2

(12) United States Patent
Otto et al.

(10) Patent No.: US 12,710,433 B2
(45) Date of Patent: Aug. 18, 2026

(54) DIAGNOSING A DISEASE ASSOCIATED WITH SYNAPTIC DEGENERATION USING AN ELISA FOR DETERMINING A BETA-SYNUCLEIN CONCENTRATION IN CSF

(71) Applicant: Markus Otto, Ulm (DE)

(72) Inventors: Markus Otto, Ulm (DE); Steffen Halbgebauer, Neu-Ulm (DE); Patrick Christian Öckl, Warthausen (DE)

(73) Assignee: Markus Otto, Ulm (DE)

( * ) Notice: Subject to any disclaimer, the term of this patent is extended or adjusted under 35 U.S.C. 154(b) by 902 days.

(21) Appl. No.: 17/893,420

(22) Filed: Aug. 23, 2022

(65) Prior Publication Data

US 2023/0071480 A1 Mar. 9, 2023

Related U.S. Application Data

(63) Continuation-in-part of application No. PCT/EP2021/054561, filed on Feb. 24, 2021.

(30) Foreign Application Priority Data

Feb. 25, 2020 (EP) .................................... 20159403

(51) Int. Cl.
*G01N 33/68* (2006.01)

(52) U.S. Cl.
CPC . *G01N 33/6896* (2013.01); *G01N 2800/2821* (2013.01); *G01N 2800/2828* (2013.01)

(58) Field of Classification Search
CPC ....... G01N 33/6896; G01N 2800/2821; G01N 2800/2828; G01N 33/543
See application file for complete search history.

(56) References Cited

U.S. PATENT DOCUMENTS

| | | | |
|---|---|---|---|
| 2005/0176078 A1 | 8/2005 | Allsop |
| 2018/0024145 A1 | 1/2018 | Sorek |
| 2019/0339291 A1 | 11/2019 | Edmonds |
| 2020/0355701 A1 | 11/2020 | Van Meter |
| 2022/0074953 A1 | 3/2022 | Van Meter |

FOREIGN PATENT DOCUMENTS

| | | |
|---|---|---|
| WO | 2018217792 A1 | 11/2018 |
| WO | 2019099732 A1 | 5/2019 |

OTHER PUBLICATIONS

Albert MS, DeKosky ST, Dickson D, Dubois B, Feldman HH, Fox NC, et al. The diagnosis of mild cognitive impairment due to Alzheimer's disease: recommendations from the National Institute on Aging-Alzheimer's Association workgroups on diagnostic guidelines for Alzheimer's disease. Alzheimers Dement. May 2011;7(3):270-9.

Storandt M, Grant EA, Miller JP, Morris JC. Longitudinal course and neuropathologic outcomes in original vs revised MCI and in pre-MCI. Neurology. Aug. 8, 2006;67(3):467-73.

Teunissen CE, Petzold A, Bennett JL, Berven FS, Brundin L, Comabella M, et al. A consensus protocol for the standardization of cerebrospinal fluid collection and biobanking. Neurology. Dec. 1, 2009;73(22):1914-22.

Bellomo G, Paolini Paoletti F, Chipi E, Petricciuolo M, Simoni S, Tambasco N, et al. A/T/(N) Profile in Cerebrospinal Fluid of Parkinson's Disease with/without Cognitive Impairment and Dementia with Lewy Bodies. Diagnostics. Nov. 26, 2020;10(12):1015.

Halbgebauer S, Steinacker P, Verde F, Weishaupt J, Oeckl P, von Arnim C, et al. Comparison of CSF and serum neurofilament light and heavy chain as differential diagnostic biomarkers for ALS. J Neurol Neurosurg Psychiatry. Jan. 2022;93(1):68-74.

Parnetti L, Gaetani L, Eusebi P, Paciotti S, Hansson O, El-Agnaf O, et al. CSF and blood biomarkers for Parkinson's disease. Lancet Neurol. 2019;18(6):573-86.

Gaetani L, Blennow K, Calabresi P, Di Filippo M, Parnetti L, Zetterberg H. Neurofilament light chain as a biomarker in heurological disorders. J Neurol Neurosurg Psychiatry. Aug. 2019;90(8):870-81.

Abu-Rumeileh S, Capellari S, Stanzani-Maserati M, Polischi B, Martinelli P, Caroppo P, et al. The CSF neurofilament light signature in rapidly progressive neurodegenerative dementias. Alzheimers Res Ther. Jan. 11, 2018;10(1):3.

Camporesi E, Nilsson J, Brinkmalm A, Becker B, Ashton NJ, Blennow K, et al. Fluid Biomarkers for Synaptic Dysfunction and Loss. Biomark Insights. Jan. 2020;15:117727192095031.

Tarawneh R, D'Angelo G, Crimmins D, Herries E, Griest T, Fagan AM, et al. Diagnostic and Prognostic Utility of the Synaptic Marker Neurogranin in Alzheimer Disease. JAMA Neurol. May 1, 2016;73(5):561-71.

Halbgebauer S, Abu-Rumeileh S, Oeckl P, Steinacker P, Roselli F, Wiesner D, et al. Blood β-Synuclein and Neurofilament Light Chain During the Course of Prion Disease. Neurology. Feb. 2, 2022;10.1212/WNL.0000000000200002.

Delaby C, Teunissen CE, Blennow K, Alcolea D, Arisi I, Amar EB, et al. Clinical reporting following the quantification of cerebrospinal fluid biomarkers in Alzheimer's disease: An international overview. Alzheimers Dement. Dec. 22, 2021.

Deckl P, Metzger F, Nagl M, von Arnim Caf, Halbgebauer S, Steinacker P, et al. Alpha-, Beta-, and Gamma-synuclein Quantification in Cerebrospinal Fluid by Multiple Reaction Monitoring Reveals Increased Concentrations in Alzheimer's and Creutzfeldt-Jakob Disease but No Alteration in Synucleinopathies. Mol Cell Proteomics. 2016;15(10):3126-38.

(Continued)

*Primary Examiner* — Olga N Chernyshev
(74) *Attorney, Agent, or Firm* — Thomas | Horstemeyer, LLP

(57) ABSTRACT

In an ex vivo method of diagnosing a disease associated with synaptic degeneration, a concentration of beta-synuclein in a cerebrospinal fluid (CSF) sample taken from a patient is determined by an enzyme-linked immunosorbent assay (ELISA).

3 Claims, 19 Drawing Sheets

(56) References Cited

OTHER PUBLICATIONS

Menendez-Gonzalez M: The many questions on the use of biomarkers for neurodegenerative diseases in clinical practice. Frontiers in aging neuroscience 2014, 6:45.
Beastall GH, Watson ID: Clinical Chemistry and Laboratory Medicine: an appreciation. Clinical chemistry and laboratory medicine 2013, 51:3-4.
Galluzzi S, Geroldi C, Amicucci G, Bocchio-Chiavetto L, Bonetti M, Bonvicini C, Cotelli M, Ghidoni R, Paghera B, Zanetti O, Frisoni GB: Supporting evidence for using biomarkers in the diagnosis of MCI due to AD. Journal of neurology 2013, 260:640-650.
Overk CR, Masliah E: Pathogenesis of synaptic degeneration in Alzheimer's disease and Lewy body disease. Biochemical pharmacology 2014, 88:508-516.
Lacor PN: Advances on the understanding of the origins of synaptic pathology in AD. Current genomics 2007, 8:486-508.
Selkoe DJ: Alzheimer's disease is a synaptic failure. Science 2002, 298:789-791.
Counts SE, Alldred MJ, Che S, Ginsberg SD, Mufson EJ: Synaptic gene dysregulation within hippocampal CA1 pyramidal neurons in mild cognitive impairment. Neuropharmacology 2014, 79:172-179.
Scheff SW, Price DA, Schmitt FA, DeKosky ST, Mufson EJ: Synaptic alterations in CA1 in mild Alzheimer disease and mild cognitive impairment. Neurology 2007, 68:1501-1508.
Scheff SW, Price DA, Schmitt FA, Mufson EJ: Hippocampal synaptic loss in early Alzheimer's disease and mild cognitive impairment. Neurobiology of aging 2006, 27:1372-1384.
Blennow K, Bogdanovic N, Alafuzoff I, Ekman R, Davidsson P: Synaptic pathology in Alzheimer's disease: relation to severity of dementia, but not to senile plaques, neurofibrillary tangles, or the ApoE4 allele. J Neural Transm (Vienna) 1996, 103:603-618.
Terry RD, Masliah E, Salmon DP, Butters N, DeTeresa R, Hill R, Hansen LA, Katzman R: Physical basis of cognitive alterations in Alzheimer's disease: synapse loss is the major correlate of cognitive impairment. Annals of neurology 1991, 30:572-580.
George JM: The synucleins. Genome biology 2002, 3:Reviews3002.
Halbgebauer S, Ockl P, Wirth K, Steinacker P, Otto M: Protein biomarkers in Parkinson's disease: Focus on cerebrospinal fluid markers and synaptic proteins. Movement disorders : official journal of the Movement Disorder Society 2016, 31:848-860.
Jakes R, Spillantini MG, Goedert M: Identification of two distinct synucleins from human brain. FEBS letters 1994, 345:27-32.
Dubois B, Feldman HH, Jacova C, Hampel H, Molinuevo JL, Blennow K, DeKosky ST, Gauthier S, Selkoe D, Bateman R, Cappa S, Crutch S, Engelborghs S, Frisoni GB, Fox NC, Galasko D, Habert MO, Jicha GA, Nordberg A, Pasquier F, Rabinovici G, Robert P, Rowe C, Salloway S, Sarazin M, Epelbaum S, de Souza LC, Vellas B, Visser PJ, Schneider L, Stern Y, Scheltens P, Cummings JL: Advancing research diagnostic criteria for Alzheimer's disease: the IWG-2 criteria. The Lancet Neurology 2014, 13:614-629.
Brooks BR, Miller RG, Swash M, Munsat TL: El Escorial revisited: revised criteria for the diagnosis of amyotrophic lateral sclerosis. Amyotrophic lateral sclerosis and other motor neuron disorders : official publication of the World Federation of Neurology, Research Group on Motor Neuron Diseases 2000, 1:293-299.
Rascovsky K, Hodges JR, Knopman D, Mendez MF, Kramer JH, Neuhaus J, van Swieten JC, Seelaar H, Dopper EG, Onyike CU, Hillis AE, Josephs KA, Boeve BF, Kertesz A, Seeley WW, Rankin KP, Johnson JK, Gorno-Tempini ML, Rosen H, Prioleau-Latham CE, Lee A, Kipps CM, Lillo P, Piguet O, Rohrer JD, Rossor MN, Warren JD, Fox NC, Galasko D, Salmon DP, Black SE, Mesulam M, Weintraub S, Dickerson BC, Diehl-Schmid J, Pasquier F, Deramecourt V, Lebert F, Pijnenburg Y, Chow TW, Manes F, Grafman J, Cappa SF, Freedman M, Grossman M, Miller BL: Rabinovici GD, Miller BL: Frontotemporal lobar degeneration: epidemiology, pathophysiology, diagnosis and management. CNS drugs 2010, 24:375-398.
Hughes AJ, Daniel SE, Kilford L, Lees AJ: Accuracy of clinical diagnosis of idiopathic Parkinson's disease: a clinico-pathological study of 100 cases. Journal of neurology, neurosurgery, and psychiatry 1992, 55:181-184.
Brown P, Brunk C, Budka H, Cervenakova L, Collie D, Green A, Ronside J, Knight R, MacKenzie J, Pergami P, Ricketts M, Summers D, Will B, Zeidler M, Zerr I: Who Manual for Surveillance of Human Transmissible Spongiform Encephalopathies Including Variant Creutzfeldt-Jakob Disease. World Health Organization, Communicable Disease Surveillance and Response 2003.
Hughes CP, Berg L, Danziger WL, Coben LA, Martin RL: A new clinical scale for the staging of dementia. The British journal of psychiatry : the journal of mental science 1982, 140:566-572.
O'Bryant SE, Waring SC, Cullum CM, Hall J, Lacritz L, Massman PJ, Lupo PJ, Reisch JS, Doody R: Staging dementia using Clinical Dementia Rating Scale Sum of Boxes scores: a Texas Alzheimer's research consortium study. Archives of neurology 2008, 65:1091-1095.
O'Bryant SE, Lacritz LH, Hall J, Waring SC, Chan W, Khodr ZG, Massman PJ, Hobson V, Cullum CM: Validation of the new interpretive guidelines for the clinical dementia rating scale sum of boxes score in the national Alzheimer's coordinating center database. Archives of neurology 2010, 67:746-749.
Litvan I, Goldman JG, Troster AI, Schmand BA, Weintraub D, Petersen RC, Mollenhauer B, Adler CH, Marder K, Williams-Gray CH, Aarsland D, Kulisevsky J, Rodriguez-Oroz MC, Burn DJ, Barker RA, Emre M: Diagnostic criteria for mild cognitive impairment in Parkinson's disease: Movement Disorder Society Task Force guidelines. Movement disorders : official journal of the Movement Disorder Society 2012, 27:349-356.
Andreasson U, Perret-Liaudet A, van Waalwijk van Doorn LJ, Blennow K, Chiasserini D, Engelborghs S, Fladby T, Genc S, Kruse N, Kuiperij HB, Kulic L, Lewczuk P, Mollenhauer B, Mroczko B, Parnetti L, Vanmechelen E, Verbeek MM, Winblad B, Zetterberg H, Koel-Simmelink M, Teunissen Ce: A Practical Guide to Immunoassay Method Validation. Frontiers in neurology 2015, 6:179.
Ingelsson M, Fukumoto H, Newell KL, Growdon JH, Hedley-Whyte ET, Frosch MP, Albert MS, Hyman BT, Irizarry MC: Early Abeta accumulation and progressive synaptic loss, gliosis, and tangle formation in AD brain. Neurology 2004, 62:925-931.
Scheff SW, Sparks L, Price DA: Quantitative assessment of synaptic density in the entorhinal cortex in Alzheimer's disease. Annals of neurology 1993, 34:356-361.
DeKosky ST, Scheff SW: Synapse loss in frontal cortex biopsies in Alzheimer's disease: correlation with cognitive severity. Annals of neurology 1990, 27:457-464.
Scheff SW, DeKosky ST, Price DA: Quantitative assessment of cortical synaptic density in Alzheimer's disease. Neurobiology of aging 1990, 11:29-37.
Masliah E, Mallory M, Alford M, DeTeresa R, Hansen LA, McKeel DW, Jr., Morris JC: Altered expression of synaptic proteins occurs early during progression of Alzheimer's disease. Neurology 2001, 56:127-129.
Irish M, Lawlor BA, Coen RF, O'Mara SM: Everyday episodic memory in amnestic mild cognitive impairment: a preliminary investigation. BMC neuroscience 2011, 12:80.
Gronholm-Nyman P, Rinne JO, Laine M: Learning and forgetting new names and objects in MCI and AD. Neuropsychologia 2010, 48:1079-1088.
Salomone S, Caraci F, Leggio GM, Fedotova J, Drago F: New pharmacological strategies for treatment of Alzheimer's disease: focus on disease modifying drugs. British journal of clinical pharmacology 2012, 73:504-517.
Davidsson P, Puchades M, Blennow K: Identification of synaptic vesicle, pre- and postsynaptic proteins in human cerebrospinal fluid using liquid-phase isoelectric focusing. Electrophoresis 1999, 20:431-437.
Davidsson P, Jahn R, Bergquist J, Ekman R, Blennow K: Synaptotagmin, a synaptic vesicle protein, is present in human cerebrospinal fluid: a new biochemical marker for synaptic pathology in Alzheimer disease? Molecular and chemical neuropathology 1996, 27:195-210.

(56) References Cited

OTHER PUBLICATIONS

Ohrfelt A, Grognet P, Andreasen N, Wallin A, Vanmechelen E, Blennow K, Zetterberg H: Cerebrospinal fluid alpha-synuclein in neurodegenerative disorders-a marker of synapse loss? Neuroscience letters 2009, 450:332-335.
Jahn H, Wittke S, Zurbig P, Raedler TJ, Arlt S, Kellmann M, Mullen W, Eichenlaub M, Mischak H, Wiedemann K: Peptide fingerprinting of Alzheimer's disease in cerebrospinal fluid: identification and prospective evaluation of new synaptic biomarkers. PloS one 2011, 6:e26540.
Brinkmalm A, Brinkmalm G, Honer WG, Frolich L, Hausner L, Minthon L, Hansson O, Wallin A, Zetterberg H, Blennow K, Ohrfelt A: SNAP-25 is a promising novel cerebrospinal fluid biomarker for synapse degeneration in Alzheimer's disease. Molecular neurodegeneration 2014, 9:53.
Zhang H, Therriault J, Kang MS, Ng KP, Pascoal TA, Rosa-Neto P, Gauthier S: Cerebrospinal fluid synaptosomal-associated protein 25 is a key player in synaptic degeneration in mild cognitive impairment and Alzheimer's disease. Alzheimer's research & therapy 2018, 10:80.
Masters CL, Bateman R, Blennow K, Rowe CC, Sperling RA, Cummings JL. Alzheimer's disease. Nat Rev Dis Primers. Oct. 15, 2015;1:15056.
Jack CR, Bennett DA, Blennow K, Carrillo MC, Dunn B, Haeberlein SB, et al. NIA-AA Research Framework: Toward a biological definition of Alzheimer's disease. Alzheimers Dement. Apr. 2018;14(4):535-62.
Sperling RA, Aisen PS, Beckett LA, Bennett DA, Craft S, Fagan AM, et al. Toward defining the preclinical stages of Alzheimer's disease: recommendations from the National Institute on Aging-Alzheimer's Association workgroups on diagnostic guidelines for Alzheimer's disease. Alzheimers Dement. May 2011;7(3):280-92.
Hampel H, Cummings J, Blennow K, Gao P, Jack CR, Vergallo A. Developing the ATX(N) classification for use across the Alzheimer disease continuum. Nat Rev Neurol. Sep. 2021;17(9):580-9.
Oeckl P, Halbgebauer S, Anderl-Straub S, von Arnim CAF, Diehl-Schmid J, Froelich L, et al. Targeted Mass Spectrometry Suggests Beta-Synuclein as Synaptic Blood Marker in Alzheimer's Disease. J Proteome Res. Mar. 6, 2020;19(3):1310-8.
Halbgebauer S, Oeckl P, Steinacker P, Yilmazer-Hanke D, Anderl-Straub S, von Arnim C, et al. Beta-synuclein in cerebrospinal fluid as an early diagnostic marker of Alzheimer's disease. J Neurol Neurosurg Psychiatry. Apr. 2021;92 (4):349-56.
Barba L, Paolini Paoletti F, Bellomo G, Gaetani L, Halbgebauer S, Oeckl P, et al. Alpha and Beta Synucleins: From Pathophysiology to Clinical Application as Biomarkers. Mov Disord. Apr. 2022;37(4):669-83.
Twohig D, Nielsen HM. α-synuclein in the pathophysiology of Alzheimer's disease. Mol Neurodegener. Jun. 11, 2019;14:23.
Milà-Alomá M, Salvadó G, Gispert JD, Vilor-Tejedor N, Grau-Rivera O, Sala-Vila A, et al. Amyloid beta, tau, synaptic, neurodegeneration, and glial biomarkers in the preclinical stage of the Alzheimer's continuum. Alzheimers Dement. Oct. 2020;16(10):1358-71.
McKhann GM, Knopman DS, Chertkow H, Hyman BT, Jack CR, Kawas CH, et al. The diagnosis of dementia due to Alzheimer's disease: recommendations from the National Institute on Aging-Alzheimer's Association workgroups on diagnostic guidelines for Alzheimer's disease. Alzheimers Dement. May 2011;7(3):263-9.

| | Calculated cut-offs [pg/ml] | Sensitivity (95% CI) [%] | Specificity (95% CI) [%] | Positive likelihood ratio |
|---|---|---|---|---|
| Ulm AD vs. NDC (Youden's index) | 542.5 | 99 (92-100) | 68 (55-79) | 3.1 |
| Ulm AD vs. NDC (best likelihood ratio) | 866.3 | 44 (32-57) | 98 (92-100) | 29 |

DIAGNOSING A DISEASE ASSOCIATED WITH SYNAPTIC DEGENERATION USING AN ELISA FOR DETERMINING A BETA-SYNUCLEIN CONCENTRATION IN CSF

CROSS REFERENCE TO RELATED APPLICATIONS

This application is a continuation-in-part to International Application PCT/EP2021/054561 entitled "Diagnosing a disease associated with synaptic degeneration using an ELISA for determining a beta-synuclein concentration in CSF", filed on Feb. 24, 2021, and claiming priority to European patent application No. 20 159 403.3 also entitled "Diagnosing a disease associated with synaptic degeneration using an ELISA for determining a beta-synuclein concentration in CSF", and filed on Feb. 25, 2020.

FIELD OF THE INVENTION

The present invention relates to an ex vivo method of diagnosing a disease associated with synaptic degeneration, the method comprising determining a concentration of beta-synuclein in a cerebrospinal fluid (CSF) sample taken from a patient. Further, the invention relates to an assay kit for determining a concentration of beta-synuclein in a cerebrospinal fluid (CSF) sample taken from a patient.

BACKGROUND

Biomarkers combined with clinical examinations do not only improve the diagnostic accuracy of neurodegenerative diseases [1-3] but are also the most promising key in helping clinicians making an accurate predictive diagnosis. Therefore, the analysis of surrogate biomarkers in the cerebrospinal fluid (CSF), reflecting specific biochemical or structural alterations in the central nervous system (CNS), is most auspicious. For Alzheimer's disease (AD) the measurement of Tau protein and the Amyloid-β peptide 1-42 (Aβ42) in the CSF, is already successfully implemented in the clinic. However, neither Tau as a general neurodegeneration marker nor Aβ42 as a marker for amyloid deposition reflect the degeneration of synapses occurring in AD. Assessing the synaptic dysfunction, which plays a major role in AD pathogenesis [4-6], could be of great benefit not only for the diagnosis but also in monitoring synaptic features of novel drug candidates in clinical trials. Moreover, synaptic loss is often preceding neuronal degeneration thereby already occurring in early AD and even patients with mild cognitive impairment (MCI) [7-9]. Additionally, the loss of synapses is better associated with cognitive deterioration than tangle and plaque pathology [10, 11]. Monitoring this loss by the analysis of a synaptic protein released into the CSF would be of great interest in the struggle for an early diagnosis and/or prognostic statement.

In 2016 a group including the inventors of this application detected a new promising marker for the analysis of synaptic loss in AD patients [12]. When measured in CSF using multiple reaction monitoring (MRM), a mass spectrometric approach, the brain-enriched protein beta-synuclein was significantly increased in AD patients compared to age matched controls. However, as the analysis then focused on the measurement of alpha-synuclein in PD patients, the number of AD patients measured was comparatively small. Furthermore, the MRM approach is very time-consuming and not feasible for most clinics.

Beta-synuclein is closely homologous to alpha-synuclein forming together with gamma-synuclein the synuclein family. The expression of beta-synuclein is primarily in the brain. More specifically in the thalamus, cerebellum, neocortex, hippocampus and striatum [13]. It is concentrated at the pre-synaptic terminal where it seems to play a role in membrane-associated processes [13-15].

There still is a need of a routine assay for diagnosing a disease associated with synaptic degeneration.

SUMMARY OF THE INVENTION

The present invention relates to an ex vivo method of diagnosing a disease associated with synaptic degeneration. The method comprises obtaining a cerebrospinal fluid (CSF) sample taken from a patient, and determining a concentration of beta-synuclein in the cerebrospinal fluid (CSF). The concentration of beta-synuclein in the cerebrospinal fluid (CSF) sample is determined by an enzyme-linked immunosorbent assay (ELISA).

The present invention further relates to an assay kit for determining a concentration of beta-synuclein in a cerebrospinal fluid (CSF) sample taken from a patient, for use in this method. The assay kit comprises a sandwich enzyme-linked immunosorbent assay (ELISA) for determining the concentration of beta-synuclein in the cerebrospinal fluid (CSF) sample. The sandwich ELISA includes capture and detection antibodies against beta-synuclein, and the capture and detection antibodies include a monoclonal capture antibody against beta- and alpha-synuclein and a detection antibody specific for beta-synuclein.

Other features and advantages of the present invention will become apparent to one with skill in the art upon examination of the following drawings and the detailed description. It is intended that all such additional features and advantages be included herein within the scope of the present invention, as defined by the claims.

BRIEF DESCRIPTION OF THE DRAWINGS

The invention can be better understood with reference to the following drawings. The components of the drawings are not necessarily to scale, emphasize instead being placed upon clearly illustrating the principles of the present invention. In the drawings, like reference numerals designate corresponding parts throughout the several views.

FIG. 2A: CSF beta-synuclein levels of all Ulmer cohorts. In total 251 CSF samples were analyzed. FIG. 2B: CSF beta-synuclein level comparison between NDC and AD subjects. Findings are shown as scatter dot plots with mean±SEM. FIG. 2C: CSF total-Tau levels of Ulmer cohort. FIG. 2D: CSF p-tau levels of Ulmer cohort. FIG. 2E: CSF Aβ42 levels of Ulmer cohorts. FIG. 2F: Serum nfL levels of Ulmer cohorts. Results are shown as box plots with median concentration, 25% and 75% percentile, and 5% and 95% whiskers Asterisks indicate significant differences between groups (*$p<0.05$, $p<0.001$, *$p<0.0001$). Serum was not available from all patients. AD, Alzheimer's disease; ALS, Amyotrophic lateral sclerosis; bvFTD, behavioral variant frontotemporal dementia; CJD, Creutzfeldt-Jakob disease; CSF, cerebrospinal fluid; DLB, Dementia with Lewy Bodies; NDC, non-demented control; PD, Parkinson's disease; PDD; Parkinson's disease dementia, p-Tau, phospho-Tau; SEM, standard error of the mean.

FIG. 3A: CSF beta-synuclein correlation to CSF total Tau (r=0.88 (CI: 0.85-0.91), p<0.0001). Patient cohorts are indicated in different gray scales. FIG. 3B: CSF beta-synuclein association to CSF p-Tau (r=0.39 (CI: 0.24-0.52), p<0.0001). FIG. 3C: CSF beta-synuclein correlation to Aβ42 (r=−0.35 (CI: −0.47−-0.21), p<0.0001). FIG. 3D: CSF beta-synulcien association to serum NfL (r=0.36 (CI: 0.21-0.49), p<0.0001). Aβ42, β-amyloid 1-42; AD, Alzheimer's disease; ALS, Amyotrophic lateral sclerosis; bvFTD, behavioral variant frontotemporal dementia; CJD, Creutzfeldt-Jakob disease; CSF, cerebrospinal fluid; NDC, non-demented control; NfL, neurofilament light chain; p-Tau, phospho Tau.

FIG. 4A: ROC analysis for the discrimination of AD vs. NDC using the Ulm cohort. Area under the curve 0.90. FIG. 4B: Calculated cut-offs for the discrimination of AD from NDC and the corresponding sensitivity and specificity as well as the positive likelihood ratio. AD, Alzheimer's disease; CSF, cerebrospinal fluid; NDC, non-demented control; ROC, receiver operating characteristics.

FIG. 6A: β-syn, FIG. 6B: α-syn, FIG. 6C: t-tau (cut-off: 404 pg/ml) and FIG. 6D: NfL levels in pre-AD (n=17), MCI-AD (n=28), dem-AD (n=30) and controls (n=35). Middle panels show FIG. 6E: β-syn, FIG. 6F: α-syn, FIG. 6G: t-tau and FIG. 6H: NfL levels in pre-AD compared to SMC-Ctrl cases (n=13). Bottom panels show the results of the receiver operating characteristic (ROC) analysis for the comparison between FIG. 6I: all AD cases (n=75) and controls, FIG. 6J: pre-AD and controls, FIG. 6K: pre-AD and SMC-Ctrl. FIG. 6L: Hypothetical trajectories of CSF β-syn, α-syn, t-tau and NfL levels along the AD continuum. Boxplots indicate median value, interquartile range and range of values. *p-values refer to the comparison between AD subgroups and controls (*p<0.05; p<0.01; *p<0.001; ****p<0.0001). +p-values refer to the comparison between MCI-AD and dem-AD with pre-AD (+p<0.05). AD: Alzheimer's disease; α-syn: α-synuclein; AUC: area under the curve; β-syn: β-synuclein; dem-AD: Alzheimer's disease with dementia; MCI-AD: Alzheimer's disease with mild cognitive impairment; NfL: neurofilament light chain protein; pre-AD: preclinical Alzheimer's disease; SMC-Ctrl: control subjects with subjective memory complaints; t-tau: total tau.

FIG. 7B: p-tau (cut-off: 56.5 pg/ml), FIG. 7C: Aβ40 and FIG. 7D: Aβ42 levels in pre-AD (n=17), MCI-AD (n=28), dem-AD (n=30) and controls (n=35). Bottom panels show receiver operating characteristic (ROC) analysis for the comparison of FIG. 7E: MCI-AD with controls and FIG. 7F: dem-AD with controls. Boxplots indicate median value, interquartile range and range of values. *p-values refer to the comparison between AD subgroups and controls (*p<0.05; *p<0.001; **p<0.0001). Aβ40: amyloid-β1-40 peptide; Aβ42: amyloid-β1-42 peptide; AD: Alzheimer's disease; α-syn: α-synuclein; AUC: area under the curve; β-syn: β-synuclein; dem-AD: Alzheimer's disease with dementia; MCI-AD: Alzheimer's disease with mild cognitive impairment; NfL: neurofilament light chain protein; pre-AD: preclinical Alzheimer's disease; p-tau: phosphorylated tau protein; t-tau: total tau protein.

DETAILED DESCRIPTION

Figure 1:
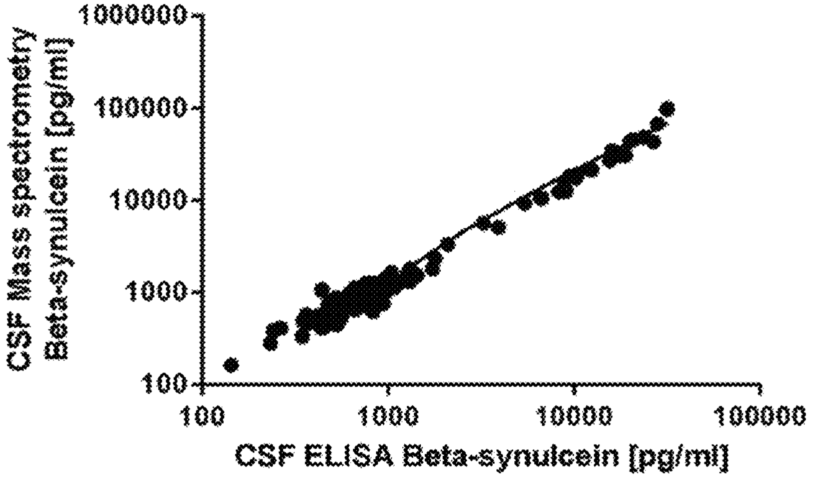
FIG. 1 is a comparison between beta-synuclein concentrations in CSF measured by ELISA and mass spectrometry over 133 samples analyzed (r=0.92 (CI: 0.89-0.94), $p<0.0001$).

The present disclosure relates to an ex vivo method of diagnosing a disease associated with synaptic degeneration, the method comprising determining a concentration of beta-synuclein in a cerebrospinal fluid (CSF) sample taken from a patient by an enzyme-linked immunosorbent assay (ELISA).

Particularly, the ELISA includes a sandwich ELISA comprising capture and detection antibodies against beta-synuclein. The capture and detection antibodies preferably include a monoclonal capture antibody against beta- and alpha-synuclein and a detection antibody specific for beta-synuclein. The detection antibody may biotynilated. A suitable detection antibody is specific for full length beta-synuclein.

The disease associated with synaptic degeneration may be differentially diagnosed against other neurodegenerative diseases, particularly against other diseases associated with synaptic degeneration.

The disease may be Alzheimer's disease (AD) or Creutzfeldt-Jakob disease (CJD) both associated with an increased level of beta-synuclein in CSF.

More particular, the disease may be Alzheimer's disease (AD) and/or Alzheimer's disease with mild cognitive impairment (AD-MCI). The increased level of beta-synuclein in CSF already appears before the cognitive impairment due to AD becomes prominent.

Generally, a suitable cut-off value for diagnosing Alzheimer's disease (AD) is in a range between 500 pg/ml and 1000 pg/ml of beta-synuclein in the cerebrospinal fluid (CSF) sample. More particular, the cut-off value may be in a range between 530 pg/ml and 920 pg/ml of beta-synuclein in the cerebrospinal fluid (CSF) sample.

A cut-off value selected for the best Youden index may be in a range between 530 pg/ml and 550 pg/ml of beta-synuclein in the cerebrospinal fluid (CSF) sample. More particular, this cut-off value may be in a range between 535 pg/ml and 545 pg/ml of beta-synuclein in the cerebrospinal fluid (CSF) sample.

A cut-off value selected for the best likelihood ratio in diagnosing AD or AD-MCI may be in a range between 850 pg/ml and 920 pg/ml of beta-synuclein in the cerebrospinal fluid (CSF) sample. More particular, this cut-off value may be in a range between 860 pg/ml and 910 pg/ml of beta-synuclein in the cerebrospinal fluid (CSF) sample.

The method may be applied for differential diagnosis of Alzheimer's disease (AD) and/or Alzheimer's disease with mild cognitive impairment (AD-MCI) against Amyotrophic lateral sclerosis (ALS). In this case, the method may additionally comprises determining the concentration of neurofilaments or neurofilament proteins in the cerebrospinal fluid (CSF) sample taken from the patient, which is typically increased with AD and ALS.

The diagnosed disease may be Creutzfeldt-Jakob disease (CJD), in which the level of beta-synuclein in CSF is increased even much stronger than in AD.

A suitable cut-off value for diagnosing Creutzfeldt-Jakob disease (CJD) is in a range between 1,000 pg/ml and 10,000 pg/ml of beta-synuclein in the cerebrospinal fluid (CSF) sample. More particular, this cut-off value may be in a range between 1,500 pg/ml and 9,000 pg/ml, or between 2,000 pg/ml and 8,000 pg/ml of beta-synuclein in the cerebrospinal fluid (CSF) sample.

The invention further relates to an assay kit for determining a concentration of beta-synuclein in a cerebrospinal fluid (CSF) sample taken from a patient. This assay kit may particularly be used in the method of the invention. The assay kit of the invention comprises a sandwich enzyme-linked immunosorbent assay (ELISA) for determining the concentration of beta-synuclein in the cerebrospinal fluid (CSF) sample. The sandwich ELISA includes capture and detection antibodies against beta-synuclein. The capture and detection antibodies include a monoclonal capture antibody against beta- and alpha-synuclein and a detection antibody specific for beta-synuclein.

Like in the method of the invention, the detection antibody may be biotynilated and/or specific for full length beta-synuclein.

Typically, the assay comprises calibrators for the concentration of beta-synuclein. These calibrators may be prepared from recombinant beta-synuclein and blocking buffer, and ranging from 10 pg/ml to at least 1,000 pg/ml. Depending on the disease to be diagnosed a calibrator of 1,000 pg/ml may be sufficient, or a calibrator of up to 10,000 pg/ml may be useful.

The method or the assay kit of the invention may be specifically be configured for assessing a status of the disease; for predicting a response to a therapy of the patient against the disease; for classifying a stage, or a prognostic stage of the patient with regard to the disease; for selecting a mode of a treatment of the patient against the disease; and/or for monitoring disease control in the patient with regard to the disease.

Figure 8:
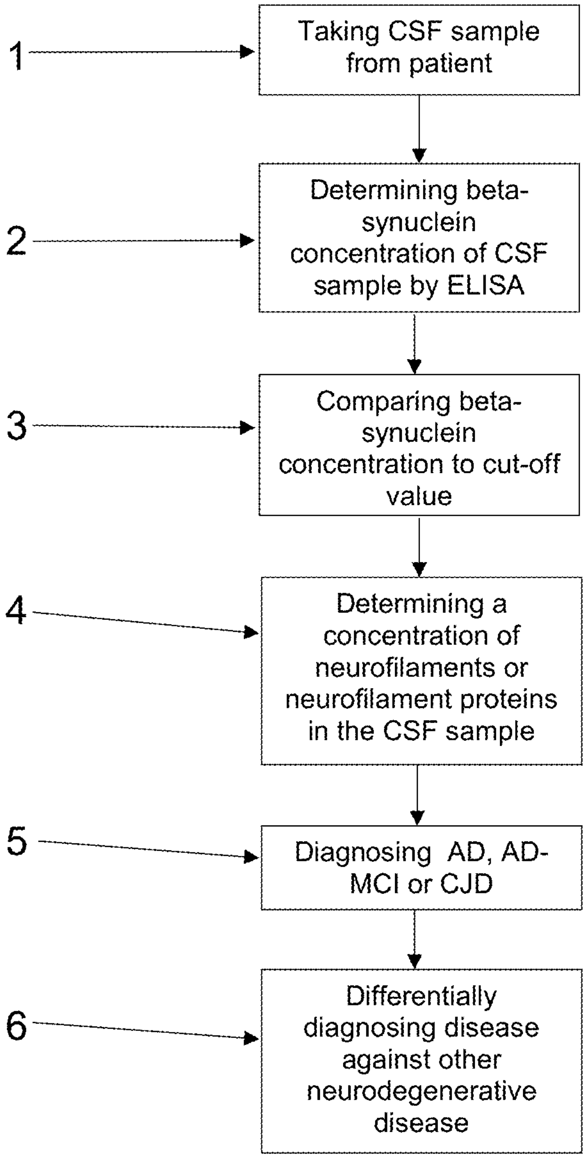
FIG. 8 is a flowchart of an ex vivo method of diagnosing a disease associated with synaptic degeneration according to the present disclosure.

Now referring in greater detail to the drawings, FIG. 8 is a flowchart of an embodiment of the ex vivo method of diagnosing a disease associated with synaptic degeneration. In step 1, a CSF sample is taken from a patient, or a CSF sample already taken from a patient is obtained. In step 2, a beta-synuclein concentration of the CSF sample is determined by an enzyme-linked immunosorbent assay (ELISA). Next, in step 3, the beta-synuclein concentration is compared to at least one cut-off value. In optional additional step 4, a concentration of neurofilaments or neurofilament proteins in the CSF sample is determined. In step 5, the obtained results are used to diagnose the disease, particularly Alzheimer's disease (AD) and/or Alzheimer's disease with mild cognitive impairment (AD-MCI) or Creutzfeldt-Jakob disease (CJD). In step 6, the respective disease is then differentially diagnosed against at least one other neurodegenerative disease.

Figure 9:
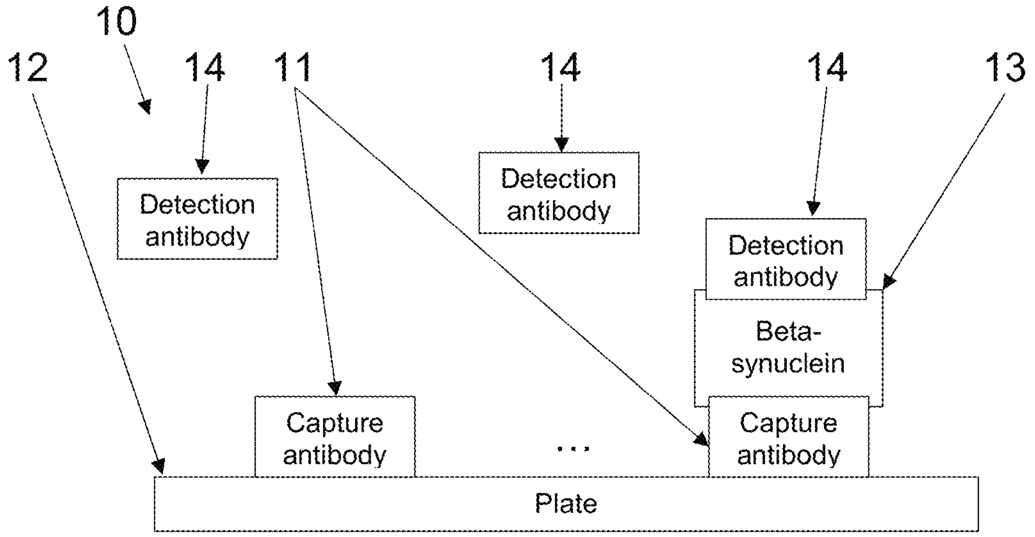
FIG. 9 illustrates a sandwich ELISA for use in the method of FIG. 8.
Figure 10:
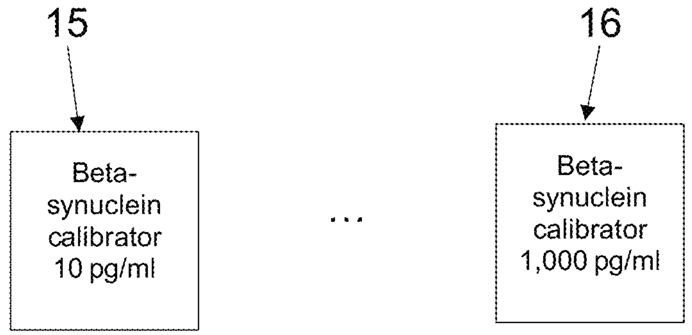
FIG. 10 illustrates calibrators to be used for calibrating the ELISA of FIG. 9.

The assay kit 10 for use in the method of FIG. 8, which is depicted in FIG. 9 includes capture antibodies 11 which are affixed to a plate 12. The capture antibodies capture beta-synuclein 13 from the CSF sample. The capture beta-synuclein 13 is then detected by detection antibodies 14 included in the assay kit 10. The assay according to FIG. 9 is called sandwich ELISA because the respective detected beta-synuclein 13 is sandwiched between one capture antibody 11 and one detection antibody 14. The detection antibodies 14 not attaching to a captured beta-synuclein are removed prior to determining the number of detection antibodies attaching to beta-synuclein 13 captured by the capture antibodies 11 affixed to the plate 12. The actual determination of the number of detection antibodies 14 is then carried out by any known method which may be applied in an ELISA. The respective process can be calibrated by means of beta-synuclein calibrators 15 and 16 according to FIG. 10 which may be included in the assay kit 10. These beta-synuclein calibrators are typically prepared from recombinant beta-synuclein and blocking buffer and range from 10 pg/ml to at least 1,000 pg/ml.

Study 1

Patients

In the study 1 leading to this application, beta-synuclein was analyzed in the CSF of 405 patients from Ulm, Gottingen. Patients from Ulm and Gottingen were divided into 6 groups according to their diagnosis; AD, Amyotrophic lateral sclerosis (ALS), behavioral variant frontotemporal dementia (bvFTD), Synucleinopathies (Parkinson's disease (PD), Dementia with Lewy bodies (DLB), Parkinson's disease dementia (PDD)), Creutzfeldt-Jakob disease (CJD) and non-demented controls (NDC).

The diagnosis of 69 AD patients from Ulm was made according to the International Working Group 2 criteria. [16]. The 29 ALS patients were diagnosed with definite or probable ALS according to the revised EI Escorial criteria [17]. bvFTD patients (n=18) were diagnosed according to the international criteria [18, 19]. 46 synucleinopathy subjects were analyzed which were diagnosed by specialists for movement disorders according to the United Kingdom PD Society Brain Bank criteria [20]. All 23 CJD patients were neuropathologically confirmed cases analyzed in the unit for transmissible spongiform encephalopathies of the Department of Neurology in Göttingen [21]. In the non-demented control cohort 65 subjects from Ulm without clinical and radiological signs for neurodegeneration (e.g. subjective complaints, tension headache, facial nerve paralysis (non-inflammatory)) were included. Furthermore, all non-demented control patients presented negative for two or more AD typical markers (total Tau>450 pg/ml, phospho-Tau (p-Tau)>61 pg/ml and Aβ42<550 pg/ml in the CSF).

The stratification of the AD cohort into patients with AD and AD with only mild cognitive impairments (MCI) was done according to the clinical dementia rating (CDR) scale [22]. For the evaluation the CDR sum of boxes (CDR SOB) was chosen [23]. Patients presenting with a CDR SOB below 2.5 were classified as AD-MCI [24]. The diagnosis of PD-MCI was made according to consensus criteria proposed by the Movement Disorder Society task force [25].

Laboratory Markers and Assay Reproducibility

Lumbar puncture was done mostly between 1 and 4 pm. CSF samples were centrifuged at 500 g and the supernatant aliquoted and frozen at −80° C. within 30 min. Serum samples for neurofilament light chain (NfL) analysis were received from peripheral blood by centrifugation (800 g, 5 min), aliquoted and stored within 2 hours at −80° C. until analysis.

Serum examination included only NfL, measured with the Simoa HD-1 platform from Quanterix (Lexington, MA, USA) using the commercially available kit. CSF analysis included the measurement of total tau, p-tau, Aβ42 (Fujirebio, Hanover, Germany) and beta-synuclein which was performed using an in-house established sandwich ELISA. CSF beta-synuclein assay-reproducibility was measured by the analysis of control samples as triplicates in four different runs. The LLOQ was determined to be the concentration corresponding to a signal of the mean blank+10SD [26]. For this purpose 16 blank values were averaged. The range of the ELISA is from 10-1000 pg/ml. Samples with values outside the range were measured again with a higher dilution. Samples were stable after up to five freeze and thaw cycles as well as for a minimum of 2 h storage at room temperature prior to processing (variability<6%).

Antibodies and Recombinant Protein

As coating antibody the monoclonal anti alpha- and beta-synuclein antibody EP1646Y BSA and Azide free (ab189217) from Abcam was used (Abcam, Cambridge, UK). For detection the monoclonal antibody EP1537Y (ab76111, Abcam, Cambridge, UK) specifically recognizing beta-synuclein was applied. The detection antibody was biotinylated in a ratio biotin to antibody 40:1 according to the biotinylation protocol provided by Quanterix (Lexington, MA, USA). The recombinant beta-synuclein was purchased from peptide (Watkinsville, GA, USA).

Beta-Synuclein Sandwich ELISA Method

For the detection of beta-synuclein in CSF a new ELISA using capture and detection antibodies against beta-synuclein was developed. Nunc Maxisorp 96 well plates were coated with a monoclonal antibody against beta- and alpha-synuclein. For each well 100 μl of antibody (3.3 pg/ml) in bicarbonate-carbonate buffer pH 9.6 (100 mM) were used. The plate was sealed with plastic wrapper and incubated overnight at 4° C. On the next day, excess fluid was removed and the wells blocked with 320 μl blocking buffer (2% BSA in PBS with 0.05% Tween) for 2 h at room temperature (RT). After removing the blocking buffer, samples were added in a 1:4 dilution with blocking buffer. Calibrators ranging from 10 to 1000 pg/ml were prepared in blocking buffer outside of the plate using recombinant beta-synuclein. 100 μl of each calibrator was added. Plates were shaken for 2 min on a small MR1 rocker (Biosan, Riga, Latvia) and then incubated at RT for 1.5 h without shaking. After sample incubation each well was washed with 300 μl washing buffer (PBS 0.05% Tween) three times. Subsequently, the previously biotinylated detection antibody specific for beta-synuclein was added. The antibody was diluted in blocking buffer and 100 μl per well were applied at a concentration of 0.66 μg/ml and incubated for 30 min at RT. After washing, 100 μl of a streptavidin-HRP (Vector laboratories, CA, USA) solution was added to each well and incubated at RT for 1 h. Excess solution was removed, the plate washed and 100 μl 3,3',5,5'-Tetramethylbenzidin (Thermo Fisher Scientific, MA, USA) added incubating for 5.5 min at RT. The reaction was stopped with 100 μl 1M Hydrochloric acid (HCL) per well. Plates were measured at 450 nm and 570 nm reference wavelength. Concentrations were obtained using a 4 parameter standard curve.

Statistical Analysis

Mann-Whitney U test was applied to determine significant differences in two groups. For comparisons of three or more groups Kruskal-Wallis test with subsequent Dunn post hoc test in case of significant results, was chosen. For cut-off calculations receiver operating characteristics (ROC) analyses were performed. Cut-off levels were selected for maximizing the Youden Index (sensitivity+specificity-1) and the best likelihood ratio. To determine significant correlations between parameters the Spearman rank correlation coefficient was used. For all analyses $p<0.05$ was considered statistically significant. Statistical calculations were performed applying the GraphPad Prism 5.0 software (GraphPad Software, La Jolla, CA, USA).

Results

Demographic and Clinical Features of the Ulm Cohort

All relevant demographic and clinical parameters are summarized in table 1. Age did not differ significantly between groups except for ALS and CJD patients which were younger compared to the AD cohort ($p<0.0001$). However, correlation analysis of all patients showed no significant association between CSF beta-synuclein levels and age (r=0.11 (CI: −0.02-0.23), p=0.09). Correlation analysis of individual cohorts displayed that only in the ALS cohort a correlation can be found (r=0.5 (CI: 0.16-0.74), p=0.0054). There was no significant difference in gender between the cohorts except for PD vs. NDC/CJD/AD and AD vs. ALS. However, sex had no effect on CSF beta-synuclein levels.

The median Mini-mental State Examination (MMSE) and CDR SOB values in the AD cohort were 23 and 3.25 respectively.

Performance of the Established Sandwich ELISA for the Detection of Beta-Synuclein in CSF The newly established assay is directed against the full length beta-synuclein protein and showed a within-run and between-run cv of 3.9% and 2.4% respectively. The LLOQ was determined to be 46.9 pg/ml. No cross-reaction with alpha- and gamma-synuclein was observed. The novel ELISA is highly correlating with an established mass spectrometric assay for the detection of beta-synuclein (r=0.92 (CI: 0.89-0.94), $p<0.0001$) as shown in FIG. 1.

Beta-Synuclein CSF Quantitation in Ulm Cohorts

Figure 2B:
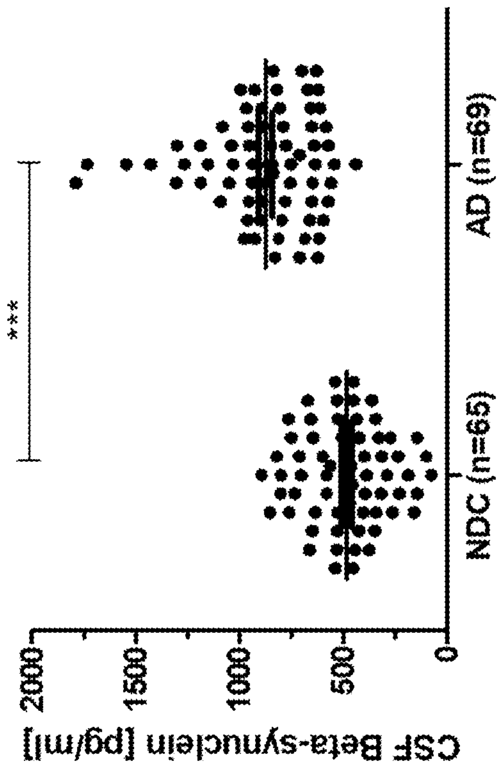
FIGS. 2A to 2F show CSF beta-synuclein ELISA results of Ulmer cohorts in comparison to routine markers.
Figure 2A:
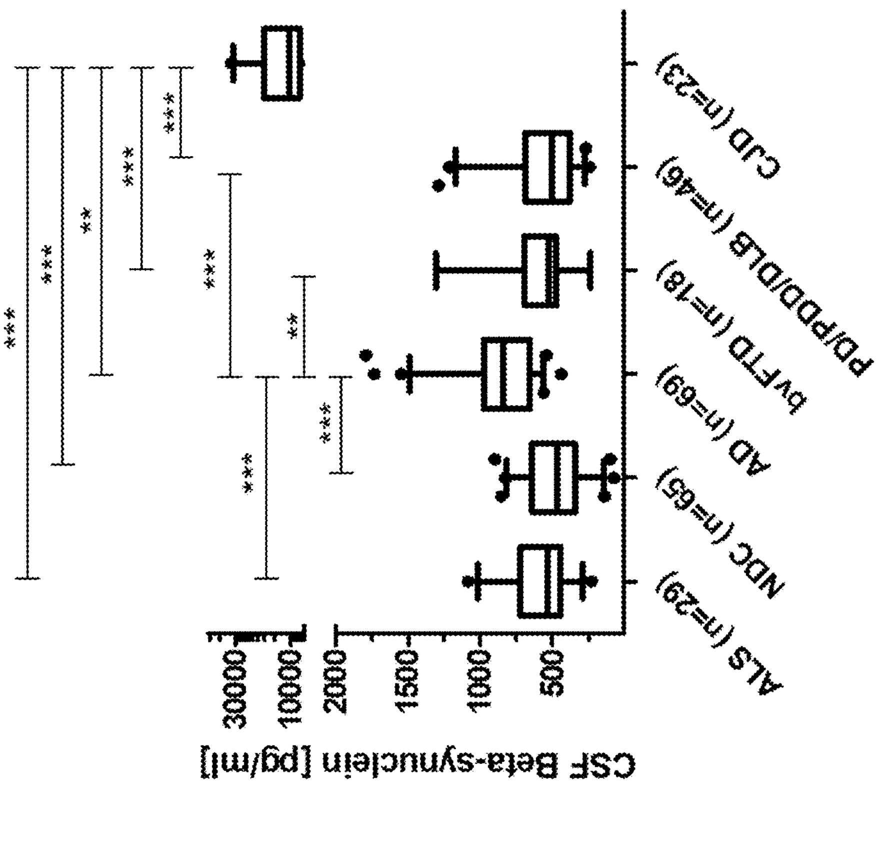
Figure 2C:
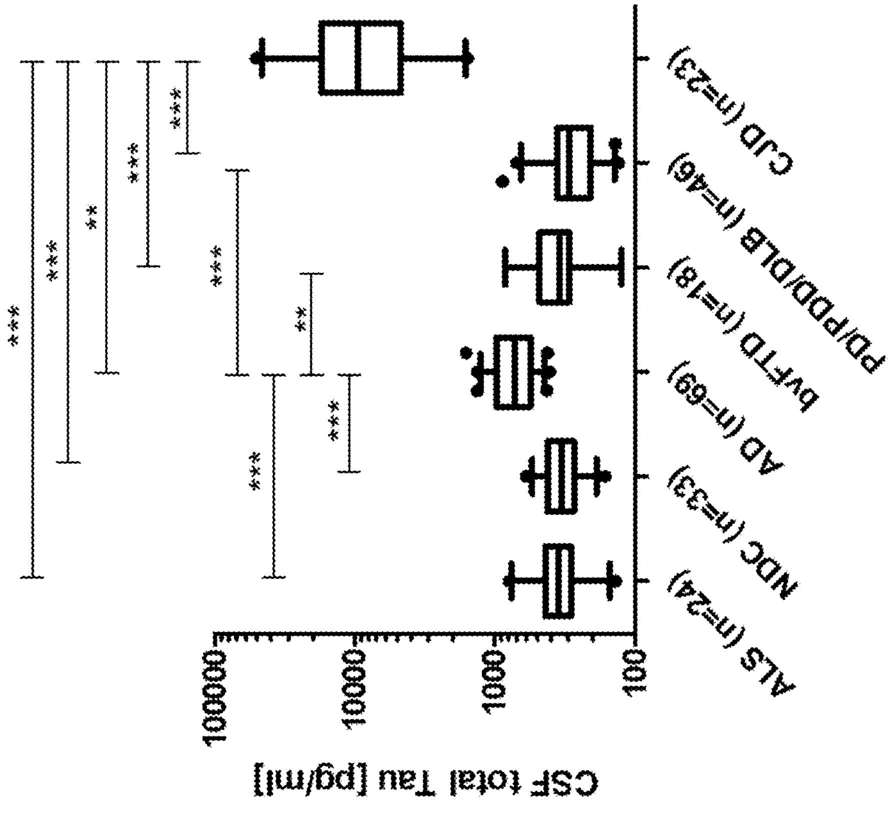
Figure 2D:
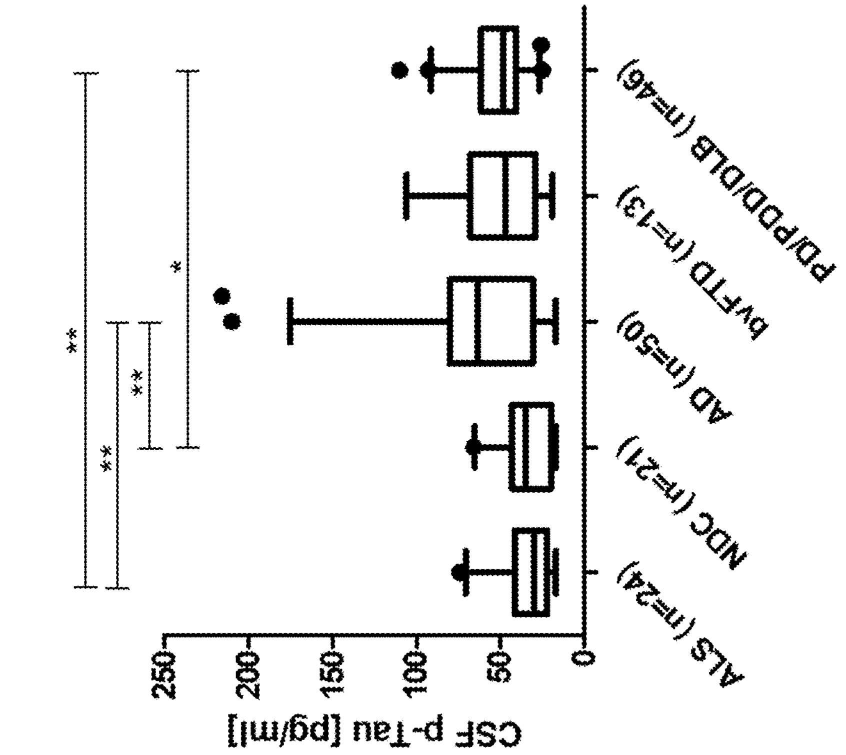
Figure 2F:
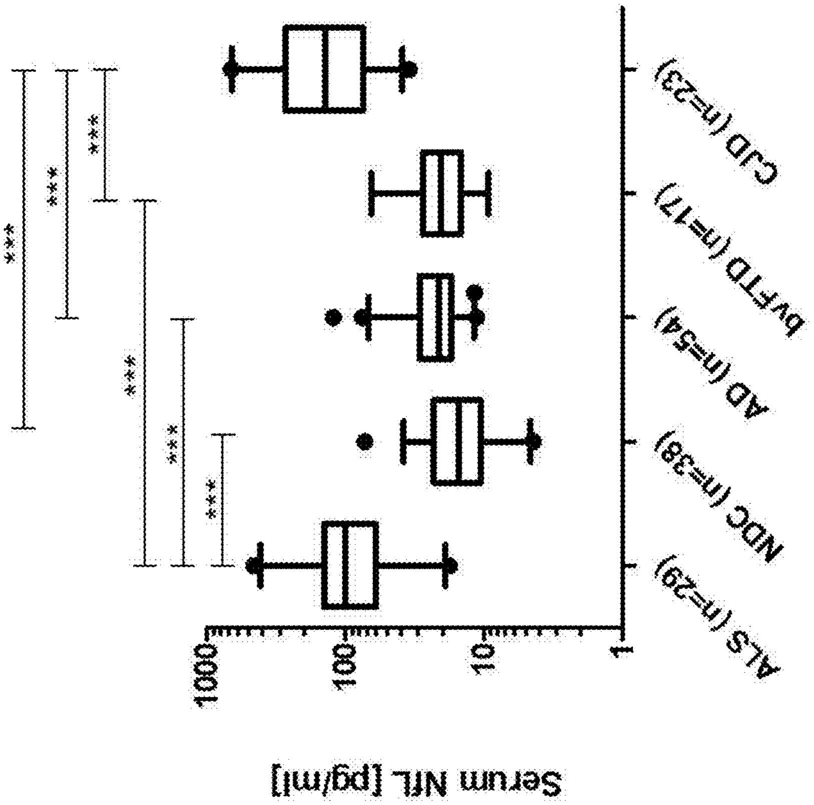
Figure 2E:
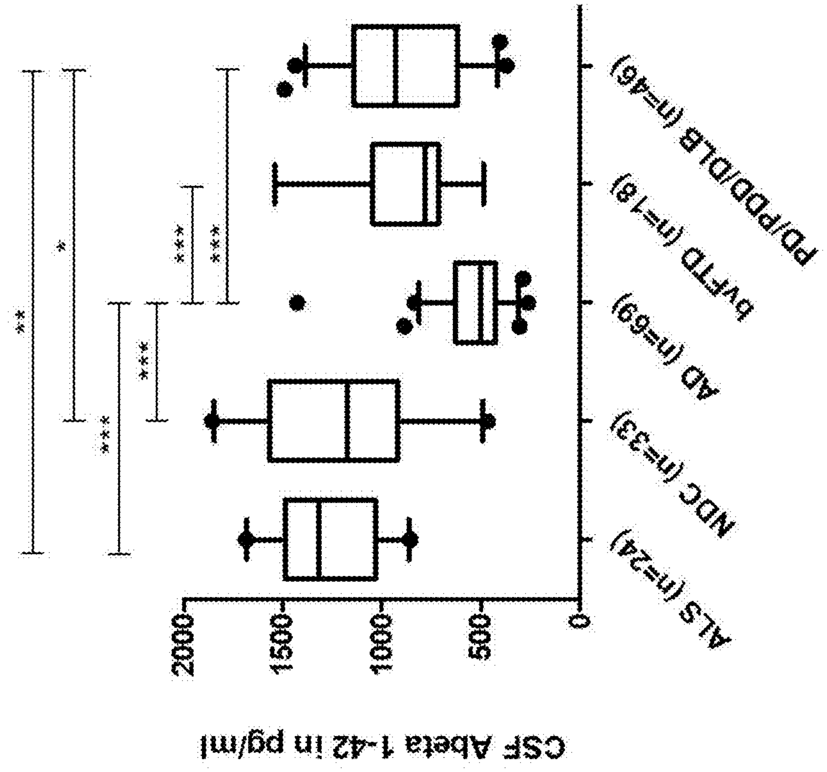

After the establishment phase and performance testing the ELISA was validated by measuring in total 227 CSF samples from Ulm thereof 69 AD, 65 NDC, 29 ALS, 18 bvFTD, 46 Synucleinopathies and 23 CJD patients from Gottingen (see FIG. 2A). The CSF beta-synuclein level of the AD group was significantly higher ($p<0.0001$) than all other groups except CJD (see table 1). CJD patients displayed the by far highest beta-synuclein levels in all cohorts. The mean AD beta-synuclein CSF value was 1.8 fold higher compared to the mean level of the NDC cohort (see FIG. 2B). In FIG. 2CF the findings of established neurochemical markers are shown for comparison.

CSF Beta-Synuclein Associations

Figure 3B:
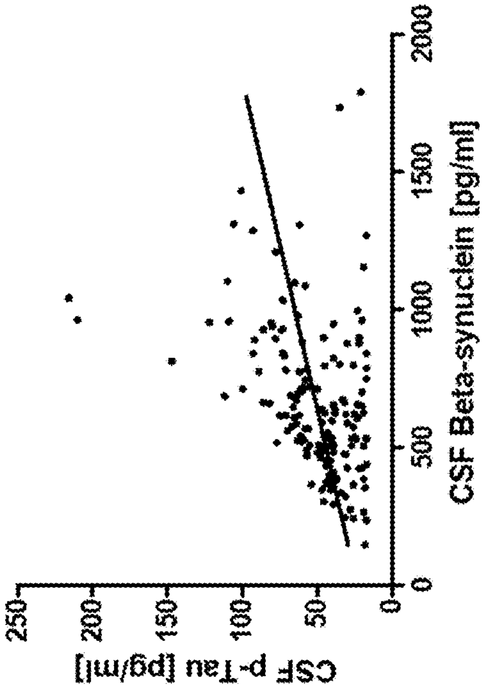
FIG. 3A to 3D illustrate CSF beta-synuclein associations to CSF total Tau and p-Tau.
Figure 3A:
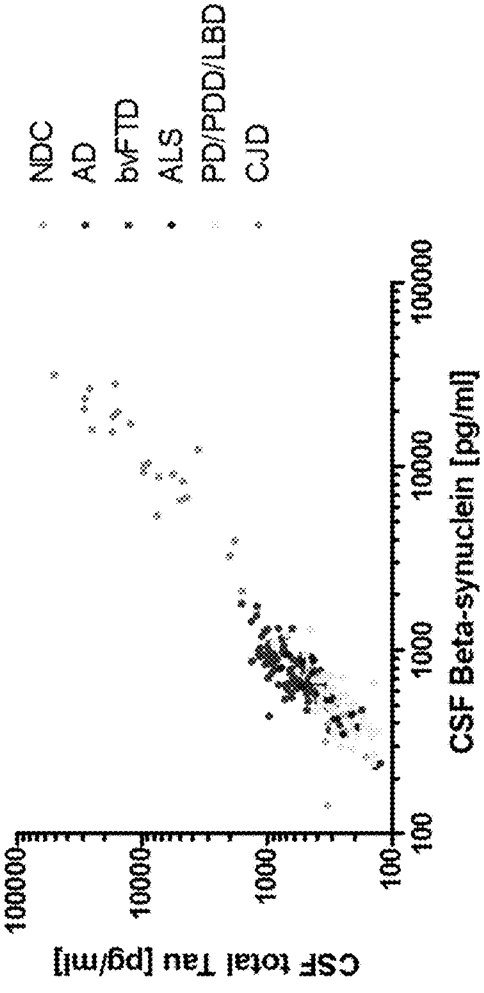
Figure 3D:
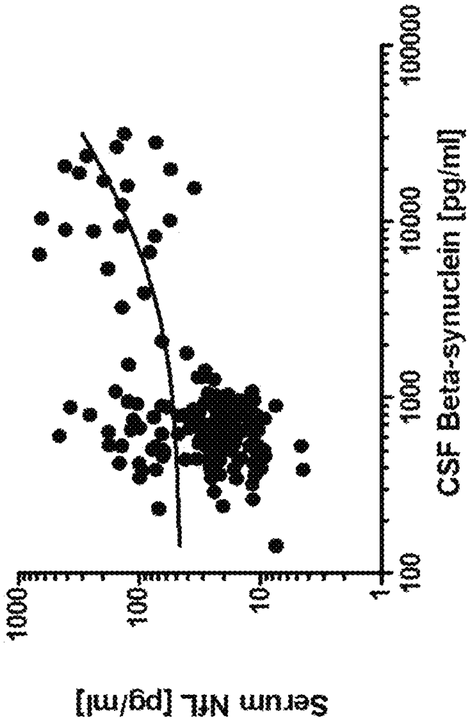
Figure 3C:
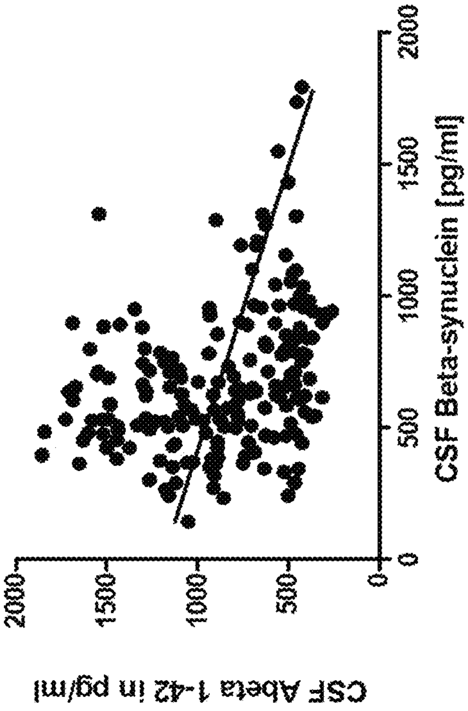

Association analysis between CSF beta-synuclein values and MMSE levels or CDR SOB revealed no correlation. Beta-synuclein CSF levels were, however, positively associated with CSF total tau (r=0.88 (CI: 0.85-0.91), $p<0.0001$) and CSF p-Tau (r=0.39 (CI: 0.24-0.52), $p<0.0001$) (see FIG. 3A and FIG. 3B). In addition, a correlation to serum NfL (r=0.36 (CI: 0.21-0.49), $p<0.0001$) and a negative association to Aβ42 (r=−0.35 (CI: −0.47–−0.21), $p<0.0001$) were also found (FIG. 3C and FIG. 3D).

Receiver Operating Characteristics

Figures 4A, 4B:
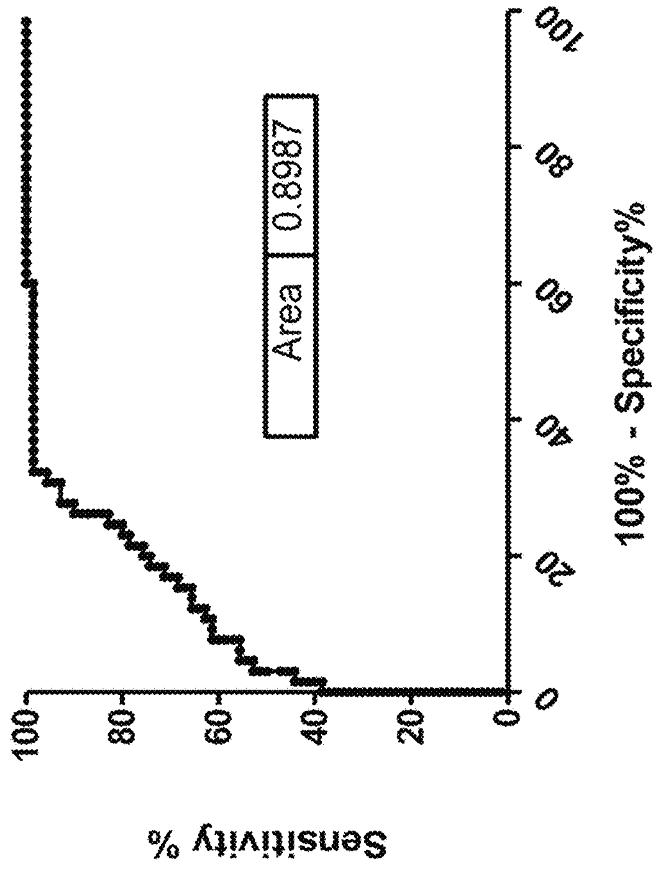
FIG. 4A to 4B shows AD and NDC CSF beta-synuclein ELISA results.

For the evaluation of the diagnostic potential of CSF beta-synuclein for discrimination between AD and NDC patients Receiver operating characteristic (ROC) analyses were performed on the Ulm cohort (see FIG. 4A). Using Youden's Index the best cut-off regarding sensitivity and specificity was calculated. Moreover, a second cut-off value with a higher selectivity (value with highest likelihood ratio) (see FIG. 4B) was selected. Applying the Ulmer cohort, patients with a CSF beta-synuclein value above the cut-off of 866.3 pg/ml have a 29 times higher chance to suffer from AD compared to subjects below the cut-off.

Analysis of CSF Beta-Synuclein as a Prognostic Marker

Figure 5:
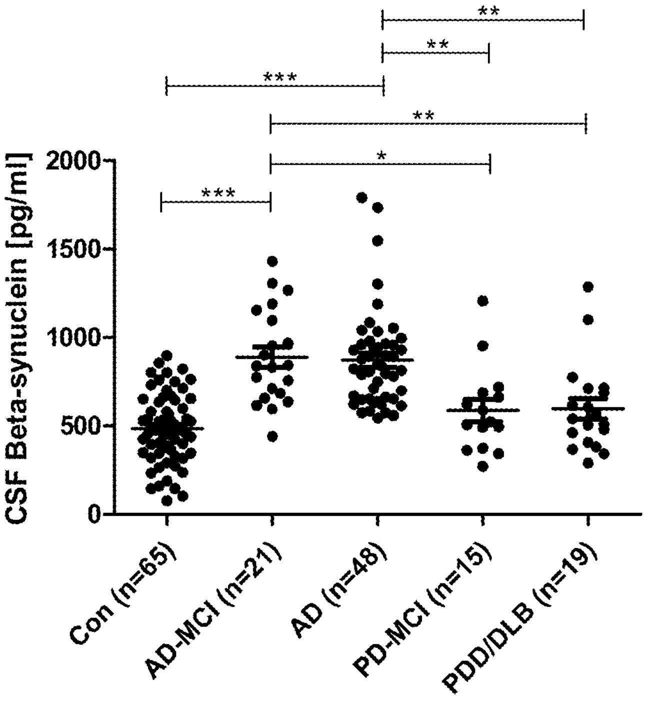
FIG. 5 shows CSF beta-synuclein ELISA results of the stratified AD and Synucleinopathy cohorts. CSF beta-synuclein levels of AD and AD-MCI patients compared to PD-MCI and PDD/DLB as well as controls. Findings are shown as scatter dot plots with mean±SEM. Asterisks indicate significant differences between groups (*p<0.05, p<0.001, *p<0.0001). AD, Alzheimer's disease; AD-MCI, AD patients with mild cognitive impairment; CSF, cerebrospinal fluid; DLB; Dementia with Lewy Bodies; NDC, non-demented control; PDD; Parkinson's disease dementia; SEM, standard error of the mean.

To evaluate if CSF beta-synuclein is already elevated in patients before the onset of dementia, the AD cohort from Ulm was stratified into patients with AD and AD-MCI and compared the CSF beta-synuclein levels with those of NDC subjects (see FIG. 5). Both AD and AD-MCI displayed statistically elevated ($p<0.0001$) beta-synuclein levels compared to the control group. Furthermore, the synucleinopathy cohort from Ulm was also stratified into patients with PD, PD-MCI and PDD/DLB. AD-MCI and AD also showed increased beta-synuclein levels compared to PD-MCI and PDD which displayed only slightly higher levels than the control cohort.

Discussion

For the diagnosis of AD various specific biomarkers such as tau and amyloid positron emission tomography or magnetic resonance imaging for the analysis of brain atrophy are validated in the clinic. Moreover, clinicians can resort to a cluster of CSF neurochemical markers reflecting for example general neurodegeneration (total tau) or the deposition of amyloid beta (Aβ42). So far, however, there is no clinically validated biomarker test for the measurement of synaptic degeneration, which is a well-established event in AD playing a major role in the early pathogenesis of the disease [27-31].

The new sandwich ELISA for the detection of beta-synuclein in CSF, a brain enriched protein concentrated in pre-synaptic terminals, has been established for the diagnosis and prediction of AD. Using the new sandwich ELISA it could be shown that CSF beta-synuclein is elevated in AD subjects compared to non-demented controls. Furthermore, the findings in more than 400 patients displayed that the increase in CSF beta-synuclein seems to be AD specific as also other neurodegenerative diseases such as ALS, bvFTD as well as synucleinopathies had lower levels. Exceptions were CJD patients which depicted the highest levels. As a rapid neurodegenerative disease, the observed high CSF beta-synuclein level in these patients was anticipated and probably due to a massive loss of neurons and thereby synapses.

CSF beta-synuclein has been found to correlate with total Tau which was to be expected as total Tau values in the CSF reflect the general degeneration of neurons comprising also synapses. The correlation coefficient was, however, not perfect showing that the two markers also differ. No association between MMSE or CDR SOB and beta-synuclein has been found. This, though, seems to be the case, not because of low beta-synuclein levels at low MMSE or high CDR SOB values but because of high CSF beta-synuclein levels throughout the whole AD cohort giving the first hint for already increased CSF beta-synuclein values in patients with only mildly decreased cognitive ability.

Performing ROC analyses and using Youden's Index revealed a specific cut-off with a sensitivity of 82% and a specificity of 73% for the discrimination of AD and controls using all available 159 AD and 131 NDC patients. Patients with a CSF beta-synuclein level above this cut-off have a 3 fold increased chance to suffer from AD. Applying a higher cut-off, the risk elevates to 34 fold.

Often patients present with only mild cognitive impairments in memory clinics. MCI can be caused by several diseases but in patients suffering mainly from episodic memory disorder (amnestic-MCI) the underlying pathology is frequently AD [32, 33]. If the results of clinical, neurochemical and neuroradiological testing are in accordance with the current guidelines for AD diagnosis these patients are also diagnosed with (prodromal) AD [16]. As synaptic dysfunction and degeneration is an early event in AD, it may be speculated that the analysis of CSF beta-synuclein may have value for the prognosis of cognitive deterioration. For testing of the predictive potential, the AD patient cohort was stratified into AD and an extra AD-MCI cohort. The findings support the hypothesis as CSF beta-synuclein levels are already increased in the AD-MCI cohort compared to control patients rendering the beta-synuclein CSF biomarker test a possible early assay for the diagnosis/prognosis of AD. As the preclinical and MCI stage of AD represent the time frame where disease-modifying agents are presumably most potent [34]. CSF beta-synuclein testing together with cognitive examinations could help stratifying clinical trial populations and select patients for treatment options. Moreover, the increase of beta-synuclein in the CSF seems be specific for AD-MCI as PD patients with MCI display no elevation. As mentioned, MCI can be caused by many dementia causing diseases and is therefore not specific for AD. This fact highlights the importance of the specificity of the CSF beta-synuclein marker for AD-MCI. Certainly, further studies comparing CSF beta-synuclein levels in more MCI patients caused by different diseases have to be performed to confirm the specificity to AD. Additionally, the findings also demonstrate that the AD cohort had significantly increased levels of CSF beta-synuclein compared to bvFTD and PDD/DLB patients who like the AD patients also suffer from dementia showing that high CSF beta-synuclein levels seem not to be selective for dementias in general.

Some other studies have been published on synaptic proteins in the CSF as markers for neurological disorders [35-38]. Many of them, however, needed to pool CSF from several patients and/or required preanalytical concentration steps and/or used mass spectrometry as readout which is, for obvious reasons, not optimal for clinical routine [35, 36]. Most prominent examples might be synaptosomal nerve-associated protein 25 (Snap-25) and neurogranin. Snap-25 can be analyzed in the CSF with IP and mass spectrometry introduced in 2014 by Brinkmalm et al. [39] and recently by an established Singulex® Erenna® immunoassay [40]. Both studies found SNAP-25 increased in AD compared to controls. Both analyses, however, need also special equipment for the measurement. Neurogranin was first quantified in CSF in 2010 by Thorsell et al. In line with the present beta-synuclein and the SNAP-25 results the colleagues also found elevated neurogranin levels in the CSF of AD patients. This supports the present evidence that beta-synuclein along with other synaptic proteins seems to be released into the CSF after degeneration of the synapse and is therefore found to be increased in the CSF of AD compared to control patients.

The strengths of this study are the establishment of a new ELISA for beta-synuclein which highly correlates with a mass spectrometric measurement of the protein, the validation of increased levels in AD compared to NDCs in samples from three different neurological centers and the analysis of further neurodegenerative diseases showing the specificity of increased beta-synuclein levels in AD with the exception of CJD. One limitation might be the non-prospective layout of the study making it difficult to analyze a potential correlation between beta-synuclein levels and synaptic loss over a period of time.

To conclude, the novel ELISA for the detection of the synaptic protein beta-synuclein in the CSF provides evidence for beta-synuclein being a new diagnostic and predictive biomarker for AD when measured in CSF. As CSF beta-synuclein levels reflect synaptic degeneration, they might also be suitable as readout in therapeutic trials targeting synaptic loss in AD.

References of Study 1

[1] Menendez-Gonzalez M: *The many questions on the use of biomarkers for neurodegenerative diseases in clinical practice*. Frontiers in aging neuroscience 2014, 6:45.
[2] Beastall G H, Watson I D: *Clinical Chemistry and Laboratory Medicine: an appreciation*. Clinical chemistry and laboratory medicine 2013, 51:3-4.
[3] Galluzzi S, Geroldi C, Amicucci G, Bocchio-Chiavetto L, Bonetti M, Bonvicini C, Cotelli M, Ghidoni R, Paghera B, Zanetti O, Frisoni G B: *Supporting evidence for using biomarkers in the diagnosis of MCI due to AD*. Journal of neurology 2013, 260:640-650.
[4] Overk C R, Masliah E: *Pathogenesis of synaptic degeneration in Alzheimer's disease and Lewy body disease*. Biochemical pharmacology 2014, 88:508-516.
[5] Lacor P N: *Advances on the understanding of the origins of synaptic pathology in AD*. Current genomics 2007, 8:486-508.
[6] Selkoe D J: *Alzheimer's disease is a synaptic failure*. Science 2002, 298:789-791.
[7] Counts S E, Alldred M J, Che S, Ginsberg S D, Mufson E J: *Synaptic gene dysregulation within hippocampal CA1 pyramidal neurons in mild cognitive impairment*. Neuropharmacology 2014, 79:172-179.
[8] Scheff S W, Price D A, Schmitt F A, DeKosky S T, Mufson E J: *Synaptic alterations in to CA1 in mild Alzheimer disease and mild cognitive impairment*. Neurology 2007, 68:1501-1508.
[9] Scheff S W, Price D A, Schmitt F A, Mufson E J: *Hippocampal synaptic loss in early Alzheimer's disease and mild cognitive impairment*. Neurobiology of aging 2006, 27:1372-1384.
[10] Blennow K, Bogdanovic N, Alafuzoff I, Ekman R, Davidsson P: *Synaptic pathology in Alzheimer's disease: relation to severity of dementia, but not to senile plaques, neurofibrillary tangles, or the ApoE4 allele*. J Neural Transm (Vienna) 1996, 103:603-618.
[11] Terry R D, Masliah E, Salmon D P, Butters N, DeTeresa R, Hill R, Hansen L A, Katzman R: *Physical basis of cognitive alterations in Alzheimer's disease: synapse loss is the major correlate of cognitive impairment*. Annals of neurology 1991, 30:572-580.
[12] Oeckl P, Metzger F, Nagl M, von Arnim C A, Halbgebauer S, Steinacker P, Ludolph A C, Otto M: *Alpha-, Beta-, and Gamma-synuclein Quantification in Cerebrospinal Fluid by Multiple Reaction Monitoring Reveals Increased Concentrations in Alzheimer's and Creutzfeldt-Jakob Disease but No Alteration in Synucleinopathies*. Molecular & cellular proteomics: MCP 2016, 15:3126-3138.
[13] George J M: *The synucleins*. Genome biology 2002, 3:REVIEWS3002.
[14] Halbgebauer S, Ockl P, Wirth K, Steinacker P, Otto M: *Protein biomarkers in Parkinson's disease: Focus on cerebrospinal fluid markers and synaptic proteins*. Movement disorders: official journal of the Movement Disorder Society 2016, 31:848-860.
[15] Jakes R, Spillantini M G, Goedert M: *Identification of two distinct synucleins from human brain*. FEBS letters 1994, 345:27-32.
[16] Dubois B, Feldman H H, Jacova C, Hampel H, Molinuevo J L, Blennow K, DeKosky S T, Gauthier S, Selkoe D, Bateman R, Cappa S, Crutch S, Engelborghs S, Frisoni G B, Fox N C, Galasko D, Habert M O, Jicha G A, Nordberg A, Pasquier F, Rabinovici G, Robert P, Rowe C, Salloway S, Sarazin M, Epelbaum S, de Souza L C, Vellas B, Visser P J, Schneider L, Stern Y, Scheltens P, Cummings J L: *Advancing research diagnostic criteria for Alzheimer's disease: the IWG-2 criteria*. The Lancet Neurology 2014, 13:614-629.
[17] Brooks B R, Miller R G, Swash M, Munsat T L: *EI Escorial revisited: revised criteria for the diagnosis of amyotrophic lateral sclerosis*. Amyotrophic lateral sclerosis and other motor neuron disorders: official publication of the World Federation of Neurology, Research Group on Motor Neuron Diseases 2000, 1:293-299.
[18] Rascovsky K, Hodges J R, Knopman D, Mendez M F, Kramer J H, Neuhaus J, van Swieten J C, Seelaar H, Dopper E G, Onyike C U, Hillis A E, Josephs K A, Boeve B F, Kertesz A, Seeley W W, Rankin K P, Johnson J K, Gorno-Tempini M L, Rosen H, Prioleau-Latham C E, Lee A, Kipps C M, Lillo P, Piguet O, Rohrer J D, Rossor M N, Warren J D, Fox N C, Galasko D, Salmon D P, Black S E, Mesulam M, Weintraub S, Dickerson B C, Diehl-Schmid J, Pasquier F, Deramecourt V, Lebert F, Pijnenburg Y, Chow T W, Manes F, Grafman J, Cappa S F, Freedman M, Grossman M, Miller B L: *Sensitivity of revised diagnostic criteria for the behavioural variant of frontotemporal dementia*. Brain: a journal of neurology 2011, 134:2456-2477.
[19] Rabinovici G D, Miller B L: *Frontotemporal lobar degeneration: epidemiology, pathophysiology, diagnosis and management*. CNS drugs 2010, 24:375-398.
[20] Hughes A J, Daniel S E, Kilford L, Lees A J: *Accuracy of clinical diagnosis of idiopathic Parkinson's disease: a clinico-pathological study of 100 cases*. Journal of neurology, neurosurgery, and psychiatry 1992, 55:181-184.
[21] Brown P, Brunk C, Budka H, Cervenakova L, Collie D, Green A, Ronside J, Knight R, MacKenzie J, Pergami P, Ricketts M, Summers D, Will B, Zeidler M, Zerr I: *WHO Manual for Surveillance of Human Transmissible Spongiform Encephalopathies Including Variant Creutzfeldt-Jakob Disease*. World Health Organization, Communicable Disease Surveillance and Response 2003.
[22] Hughes C P, Berg L, Danziger W L, Coben L A, Martin R L: *A new clinical scale for the staging of dementia*. The British journal of psychiatry: the journal of mental science 1982, 140:566-572.
[23] O'Bryant S E, Waring S C, Cullum C M, Hall J, Lacritz L, Massman P J, Lupo P J, Reisch J S, Doody R: *Staging dementia using Clinical Dementia Rating Scale Sum of Boxes scores: a Texas Alzheimer's research consortium study*. Archives of neurology 2008, 65:1091-1095.
[24] O'Bryant S E, Lacritz L H, Hall J, Waring S C, Chan W, Khodr Z G, Massman P J, Hobson V, Cullum C M: *Validation of the new interpretive guidelines for the clinical dementia rating scale sum of boxes score in the national Alzheimer's coordinating center database*. Archives of neurology 2010, 67:746-749.
[25] Litvan I, Goldman J G, Troster A I, Schmand B A, Weintraub D, Petersen R C, Mollenhauer B, Adler C H, Marder K, Williams-Gray C H, Aarsland D, Kulisevsky J, Rodriguez-Oroz M C, Burn D J, Barker R A, Emre M: *Diagnostic criteria for mild cognitive impairment in Parkinson's disease: Movement Disorder Society Task Force guidelines*. Movement disorders: official journal of the Movement Disorder Society 2012, 27:349-356.
[26] Andreasson U, Perret-Liaudet A, van Waalwijk van Doom L J, Blennow K, Chiasserini D, Engelborghs S, Fladby T, Genc S, Kruse N, Kuiperij H B, Kulic L, Lewczuk P, Mollenhauer B, Mroczko B, Parnetti L, Vanmechelen E, Verbeek M M, Winblad B, Zetterberg H, Koel-Simmelink M, Teunissen C E: *A Practical Guide to Immunoassay Method Validation*. Frontiers in neurology 2015, 6:179.

[27] Ingelsson M, Fukumoto H, Newell K L, Growdon J H, Hedley-Whyte E T, Frosch M P, Albert M S, Hyman B T, Irizarry M C: *Early Abeta accumulation and progressive synaptic loss, gliosis, and tangle formation in AD brain*. Neurology 2004, 62:925-931.

[28] Scheff S W, Sparks L, Price D A: *Quantitative assessment of synaptic density in the entorhinal cortex in Alzheimer's disease*. Annals of neurology 1993, 34:356-361.

[29] DeKosky S T, Scheff S W: *Synapse loss in frontal cortex biopsies in Alzheimer's disease: correlation with cognitive severity*. Annals of neurology 1990, 27:457-464.

[30] Scheff S W, DeKosky S T, Price D A: *Quantitative assessment of cortical synaptic density in Alzheimer's disease*. Neurobiology of aging 1990, 11:29-37.

[31] Masliah E, Mallory M, Alford M, DeTeresa R, Hansen L A, McKeel D W, Jr., Morris J C: *Altered expression of synaptic proteins occurs early during progression of Alzheimer's disease*. Neurology 2001, 56:127-129.

[32] Irish M, Lawlor B A, Coen R F, O'Mara S M: *Everyday episodic memory in amnestic mild cognitive impairment: a preliminary investigation*. BMC neuroscience 2011, 12:80.

[33] Gronholm-Nyman P, Rinne J O, Laine M: *Learning and forgetting new names and objects in MCI and AD*. Neuropsychologia 2010, 48:1079-1088.

[34] Salomone S, Caraci F, Leggio G M, Fedotova J, Drago F: *New pharmacological strategies for treatment of Alzheimer's disease: focus on disease modifying drugs*. British journal of clinical pharmacology 2012, 73:504-517.

[35] Davidsson P, Puchades M, Blennow K: *Identification of synaptic vesicle, pre- and postsynaptic proteins in human cerebrospinal fluid using liquid-phase isoelectric focusing*. Electrophoresis 1999, 20:431-437.

[36] Davidsson P, Jahn R, Bergquist J, Ekman R, Blennow K: *Synaptotagmin, a synaptic vesicle protein, is present in human cerebrospinal fluid: a new biochemical marker for synaptic pathology in Alzheimer disease*? Molecular and chemical neuropathology 1996, 27:195-210.

[37] Ohrfelt A, Grognet P, Andreasen N, Wallin A, Vanmechelen E, Blennow K, Zetterberg H: *Cerebrospinal fluid alpha-synuclein in neurodegenerative disorders-a marker of synapse loss*? Neuroscience letters 2009, 450:332-335.

[38] Jahn H, Wittke S, Zurbig P, Raedler T J, Arlt S, Kellmann M, Mullen W, Eichenlaub M, Mischak H, Wiedemann K: *Peptide fingerprinting of Alzheimer's disease in cerebrospinal fluid: identification and prospective evaluation of new synaptic biomarkers*. PloS one 2011, 6:e26540.

[39] Brinkmalm A, Brinkmalm G, Honer W G, Frolich L, Hausner L, Minthon L, Hansson O, Wallin A, Zetterberg H, Blennow K, Ohrfelt A: *SNAP-25 is a promising novel cerebrospinal fluid biomarker for synapse degeneration in Alzheimer's disease*. Molecular neurodegeneration 2014, 9:53.

[40] Zhang H, Therriault J, Kang M S, Ng K P, Pascoal T A, Rosa-Neto P, Gauthier S: *Cerebrospinal fluid synaptosomal-associated protein 25 is a key player in synaptic degeneration in mild cognitive impairment and Alzheimer's disease*. Alzheimer's research & therapy 2018, 10:80.

Study 2

The neuropathological changes underlying Alzheimer's disease (AD), namely brain deposition of amyloid-β (Aβ) and phosphorylated tau (p-tau) aggregates, are supposed to start 15-20 years before the appearance of clinical manifestations (1). According to the A/T/(N) classification system, such events can be detected in vivo by reduced $A\beta_{1-42}/A\beta_{1-40}$ ratio (Aβ42/40) and increased p-tau levels in the cerebrospinal fluid (CSF), respectively (2). The preclinical stage of AD (pre-AD) identifies those subjects who are still cognitively unimpaired but already show AD-related changes in CSF (2,3). Given the potential benefits of early pharmacological intervention, the pre-AD phase might represent the best time window for clinical trials. It is, thus, fundamental to characterize all phenomena occurring in AD pathophysiology, including those pathways not assessed within the A/T/(N) system, such as synaptic dysfunction, which may occur years before neuronal death (4,5).

β-synuclein (β-syn) is a promising candidate biomarker for synaptic damage, and its CSF levels are reported markedly elevated in AD patients, at similar extents at the dementia (dem-AD) and mild cognitive impairment stages (MCI-AD) (6-8). Here, the aim was to to investigate CSF β-syn levels in cognitively healthy subjects (non-degenerative neurological patients and subjects with subjective cognitive complaints) and in the whole AD continuum, including pre-AD cases. Given their close pathophysiological relationship, CSF β-syn values were compared with those of α-synuclein (α-syn), another synaptic protein which has been variably reported to be increased in AD (9-11). Moreover, two surrogate biomarkers of neuro-axonal degeneration were assessed, namely total tau protein (t-tau) and neurofilament light chain protein (NfL), in order to better describe the evolution of synaptic and neuronal damage in the AD continuum.

Methods

Patients

The study cohort comprised 110 subjects (AD n=75, controls n=35), consecutively enrolled at the Section of Neurology in Perugia (University of Perugia, Perugia, Italy) from 2015 to 2020. AD patients underwent, at baseline, a thorough neuropsychological evaluation, morphologic brain imaging and lumbar puncture (LP) as a part of their diagnostic work-up. Diagnosis of AD was based on the CSF profile (A+/T+) according to most updated National Institute on Ageing and Alzheimer's Association (NIA-AA) recommendations (2,3,12,13). The Clinical Dementia Rating scale (CDR) was used to assess the functional impact of cognitive symptoms (14). Based neuropsychological testing and CDR, AD patients were classified into three groups. Pre-AD subjects (n=17) were individuals referring for subjective cognitive complaints, in which the neuropsychological evaluation did not meet the criteria for MCI (3,13). MCI-AD (n=28) and dem-AD groups (n=30) included patients having a CDR score=0.5 and 1.0, respectively (3,12,13).

The control group (n=35) included 13 subjects with subjective memory complaints (SMC-Ctrl), who did not meet the criteria for MCI, and 22 cognitively unimpaired patients affected by non-degenerative neurological conditions (Dis-Ctrl, see Table 1 legend for diagnoses). LP was performed in all control subjects as a part of the diagnostic work up. CSF AD core biomarkers were within the normal range in each case, thus allowing to exclude AD pathology (Table 1). No control subject showed cognitive impairment after at least 2 years of follow-up.

CSF Sampling and Analysis

Following standardized international guidelines (15), 10-12 ml CSF were collected from each subject, centrifuged at 2000 g×10' and stored at −80° until use. CSF AD core biomarkers (Aβ40, Aβ42, p-tau and t-tau) were measured in Perugia (Italy) by means of Lumipulse G600-II system (Fujirebio Europe, Gent, Belgium). The cut-off values were 0.069, 56.5 pg/ml and 404 pg/ml for Aβ42/40, p-tau and t-tau, respectively (16). CSF α-syn and β-syn were measured in Ulm (Germany) using a commercial α-syn immunoassay (Euroimmun, Lubeck, Germany) and a recently described immunoassay for β-syn (8), respectively. CSF NfL quantification was performed in Halle (Germany) with a commercially available kit for the ELLA microfluidic system (Bio-Techne, Minneapolis, USA) (17). The coefficients of intra- and inter-assay variability for all measurements were <10% and <15%, respectively.

Statistical Analysis

Statistical analysis was performed using R software version 3.5.1 (R Studio, Boston, USA) and GraphPad 7 (GraphPad Software, La Jolla, USA). The $\chi^2$ test and the Mann-Whitney test were used to compare categorical and continuous variables between two groups, respectively. For multiple testing, analysis of covariance (ANCOVA) with adjustment for age was adopted, followed by Bonferroni's post-hoc correction. Correlations between biomarker levels with the Spearman's correlation coefficient, and the best cut-off levels for each biomarker by maximizing the Youden's index were calculated. The diagnostic performance of biomarkers was assessed through receiver operating characteristic (ROC) analyses, which have been age and/or sex-adjusted, if necessary, by means of multiple logistic regression. ROC curves were compared with DeLong test (Supplement). All analyses were considered statistically significant with p-values<0.05.

Results

CSF Biomarkers in AD Continuum

Table 1 shows demographic and biochemical data of the study population. In comparison to controls, AD patients showed increased CSF β-syn, α-syn, t-tau and NfL levels (p<0.0001 for all comparisons). β-syn and t-tau concentrations were significantly increased in all AD subgroups, namely pre-AD, MCI-AD and dem-AD, compared to controls (p<0.001 for all comparisons). Differently, only pre-AD cases showed higher α-syn (p=0.02) and only dem-AD patients higher NfL levels than controls (p=0.001) (FIG. 6A to 6D). No difference was found in CSF levels of Aβ40, Aβ42, Aβ42/40 ratio, p-tau, NfL, β-syn and α-syn among AD subgroups, while t-tau concentrations were higher in MCI-AD and dem-AD compared to pre-AD (p=0.04 and p=0.01, respectively) (FIG. 6D, FIG. 7A to 7F). In AD patients, CSF β-syn showed significant associations with α-syn (r=0.69, p<0.0001), t-tau (r=0.40, p=0.0004) and NfL levels (r=0.32, p=0.005). Moreover, β-syn correlated better with t-tau than with NfL in pre-AD cases (r=0.88, p<0.0001; r=0.59, p=0.01, respectively) (biomarker correlation analyses in Table S1).

TABLE 1

Demographical and biochemical data of the study cohort.

| | Controls | | | AD continuum | | | |
|---|---|---|---|---|---|---|---|
| | total | Dis-Ctrl* | SMC-Ctrl | total | pre-AD | MCI-AD | dem-AD |
| N. of patients (f/m) | 35 (14/21) | 22 (11/11) | 13 (3/10) | 75 (51/24) | 17 (13/4) | 28 (17/11) | 30 (21/9) |
| Age at LP | 64.9 (±8.8) | 64.6 (±8.8) | 65.3 (±9.2) | 72.6 (±5.9) | 72.6 (±5.7) | 71.6 (±4.9) | 73.5 (±6.8) |
| A+/T+/N+ | 0/0/0 | 0/0/0 | 0/0/0 | 75/75/67 | 1 7/17/10 | 28/28/27 | 30/30/30 |
| β-syn | 206 | 212 | 180 | 649 | 658 | 652 | 612 |
| α-syn | (162-263) | (169-276) | (142-256) | (395-845) | (569-893) | (356-828) | (359-777) |
| | 1435 | 1537 | 1130 | 1992 | 2225 | 2069 | 1782 |
| | (1186-1838) | (1274-1870) | (1005-1766) | (1523-2506) | (1631-2731) | (1570-2412) | (1500-2453) |
| t-tau | 262 (162-307) | 287 (254-335) | 179 (153-243) | 653 (544-894) | 447 (346-620) | 705 (547-889) | 720 (582-978) |
| NfL | 604 (409-892) | 651 (573-896) | 458 (341-641) | 1099 (845-1787) | 857 (709-954) | 1110 (822-1335) | 1286 (954-2080) |
| Aβ40 | 8910 (6663-13089) | 12697 (10954-14436) | 6560 (6145-7327) | 12952 (8970-15838) | 12238 (8439-15003) | 14453 (10731-16775) | 12360 (8722-15543) |
| Aβ42 | 1124 (790-1354) | 1330 (1186-1450) | 759 (674-976) | 619 (470-796) | 645 (542-687) | 633 (498-781) | 555 (418-829) |
| Aβ42/40 | 0.103 (0.096-0.126) | 0.103 (0.099-0.123) | 0.100 (0.091-0.134) | 0.051 (0.045-0.059) | 0.056 (0.051-0.062) | 0.045 (0.040-0.058) | 0.050 (0.046-0.058) |
| p-tau | 41.1 (34.0-47.5) | 45.4 (41.0-48.6) | 33.0 (29.0-39.0) | 86.0 (69.0-119.0) | 64.1 (60.0-88.0) | 90.3 (72.5-117.7) | 88.4 (70.2-119.6) |

Age is reported in years at the time of LP (mean±standard deviation). Biomarker levels are reported in pg/ml (except Aβ42/40 ratio) as median (interquartile range). *Clinical diagnoses: 3 seizures, 3 cerebrovascular diseases, 5 psychiatric disorders, 5 optic neuritis, 6 polyneuropathies.

Abbreviations. Aβ40: amyloid-$\beta_{1-40}$ peptide; Aβ42: amyloid-$\beta_{1-42}$ peptide; AD: Alzheimer's disease; α-syn: α-synuclein; β-syn: β-synuclein; dem-AD: Alzheimer's disease with dementia; Dis-Ctrl: disease controls; LP: lumbar puncture; MCI-AD: Alzheimer's disease with mild cognitive impairment; NfL: neurofilament light chain protein; pre-AD: preclinical Alzheimer's disease; p-tau: phosphorylated tau protein; t-tau: total tau protein.

Comparison Between Pre-AD and SMC-Ctrl

After stratification of controls into Dis-Ctrl and SMC-Ctrl subgroups, no difference in any CSF biomarker levels was found except for higher t-tau in Dis-Ctrl (p=0.02). CSF β-syn and t-tau levels were significantly higher in pre-AD compared to SMC-Ctrl subjects ($p<0.0001$ and $p=0.004$, respectively). Moreover, pre-AD cases showed increased α-syn ($p=0.004$) and NfL levels ($p=0.03$), but significance did not survive to age-adjustment and Bonferroni correction (FIG. 6E to 6H).

Diagnostic Performance of CSF β-Syn in AD Continuum

Complete results of ROC analysis are reported in Table S2. CSF β-syn discriminated AD patients from controls with high accuracy (area under the curve, AUC: 0.91) and, in particular, showed an optimal performance in the discrimination between pre-AD versus controls (AUC: 0.97) and versus SMC-Ctrl (AUC: 0.99). β-syn remained a significant independent predictor of AD/pre-AD diagnosis even after adjustment for age and sex in multiple regression models (Supplement). As a comparison, t-tau had a similar discriminating performance, while α-syn and NfL yielded suboptimal accuracy (FIGS. 6I to 6K, FIGS. 7A to 7F). By maximizing the Youden's index, the best cut-off for CSF β-syn for the comparison between AD and control subjects (>313 pg/ml) were calculated. By applying this cut-off, β-syn showed an excellent accuracy in the discrimination of pre-AD subjects from all controls (sensitivity: 100.0%, specificity: 82.5%) and from SMC-Ctrl (sensitivity: 94.1%, specificity: 84.6%). Of interest, all pre-AD cases with normal CSF t-tau levels (A+/T+/N− profile, n=7) showed β-syn values above the chosen cut-off.

Discussion

β-syn is emerging as a CSF biomarker for synaptic damage in AD, being increased in both dementia and predementia phases (6-8). In the present study, the remarkable increase of CSF β-syn in all stages of AD continuum and a robust diagnostic value for the identification of subjects with AD pathology, even in the preclinical phase, were described. Indeed, β-syn levels were elevated in pre-AD cases to a similar extent than patients showing MCI and dementia (8).

Increased CSF α-syn levels in pre-AD subjects were also observed, but not in MCI-AD and dem-AD. While α-syn has been variably reported increased in AD as a CSF biomarker of synaptic derangement, decreased α-syn levels may indicate the presence of α-synucleinopathy (9,18). In the cohort of this study, one may speculate that the slight decrease of CSF α-syn along the AD continuum could partly depend on α-syn co-pathology, which is reported in nearly half of all AD cases (10). Elevated CSF levels of both β-syn and α-syn may, hence, reflect the earliest synaptic dysfunction occurring in AD. Given that β-syn concentrations are not influenced by the presence of synucleinopathy nor by blood contamination, which instead affects α-syn measurements, CSF β-syn might be an even more robust synaptic biomarker than α-syn (9).

Figure 6A:
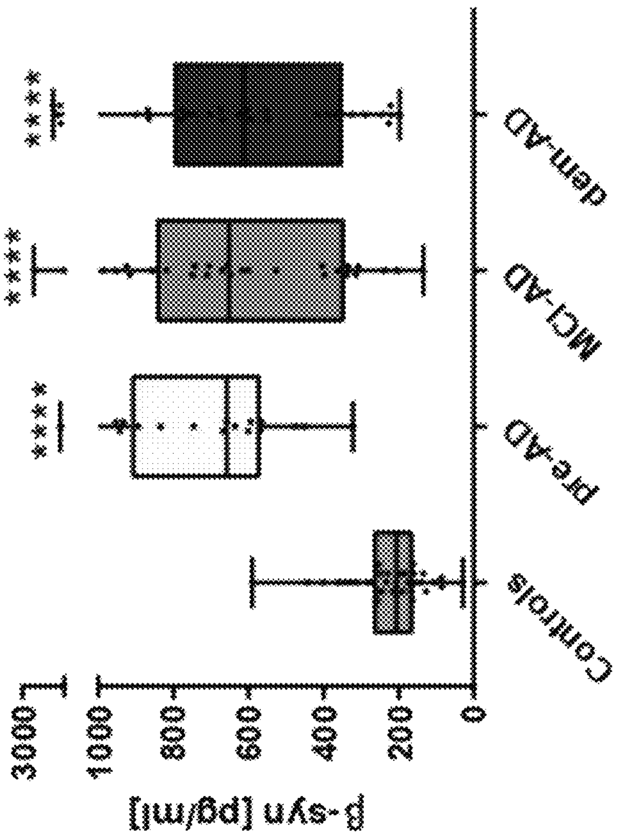
FIG. 6A to 6L illustrate cerebrospinal fluid biomarker levels in AD continuum. Top panels show
Figure 6B:
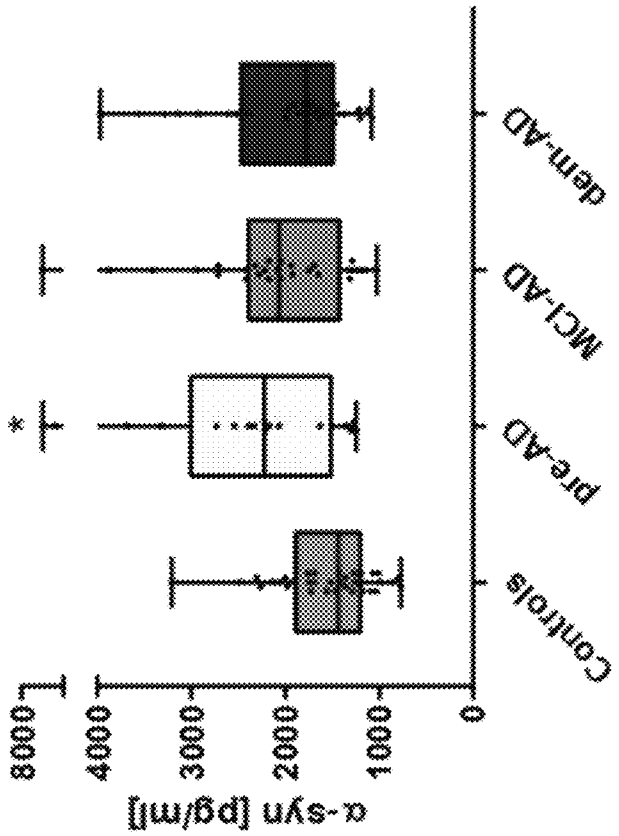
Figure 6D:
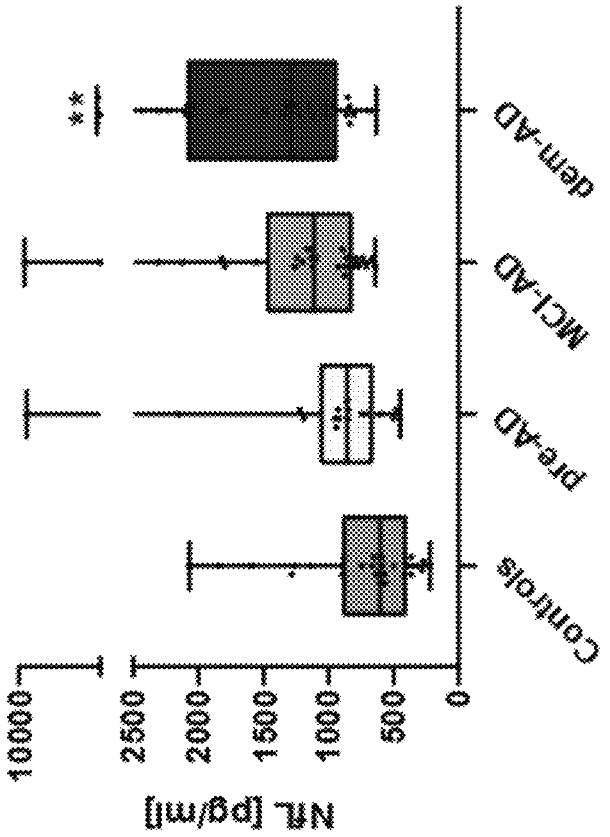
Figure 6C:
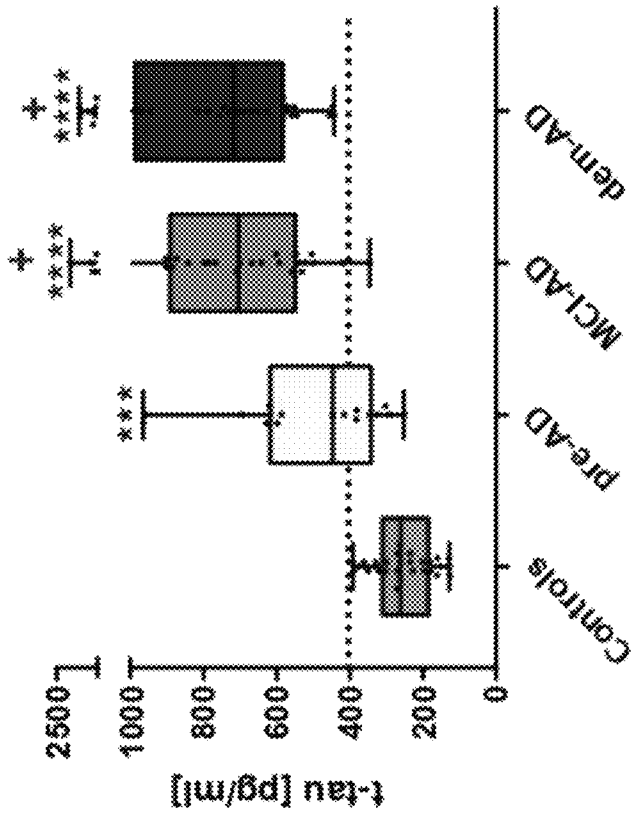
Figure 6E:
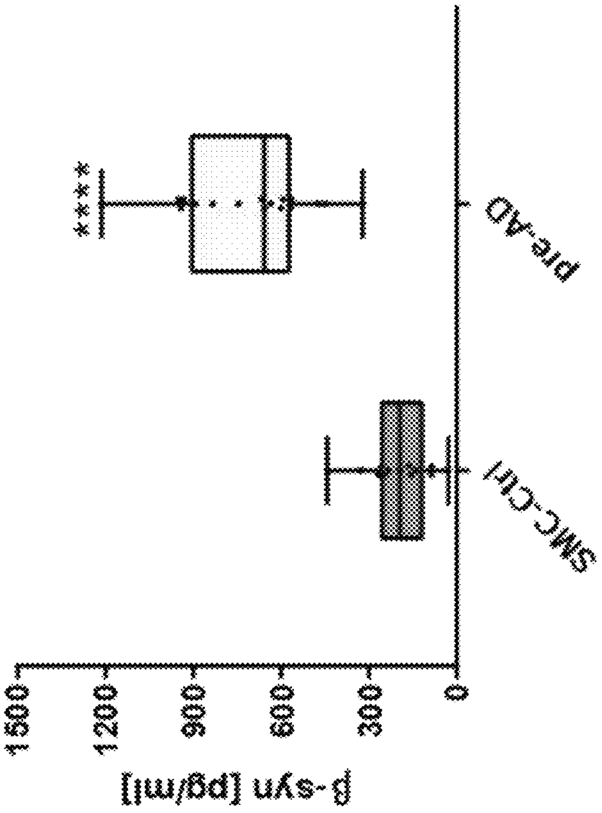
Figure 6F:
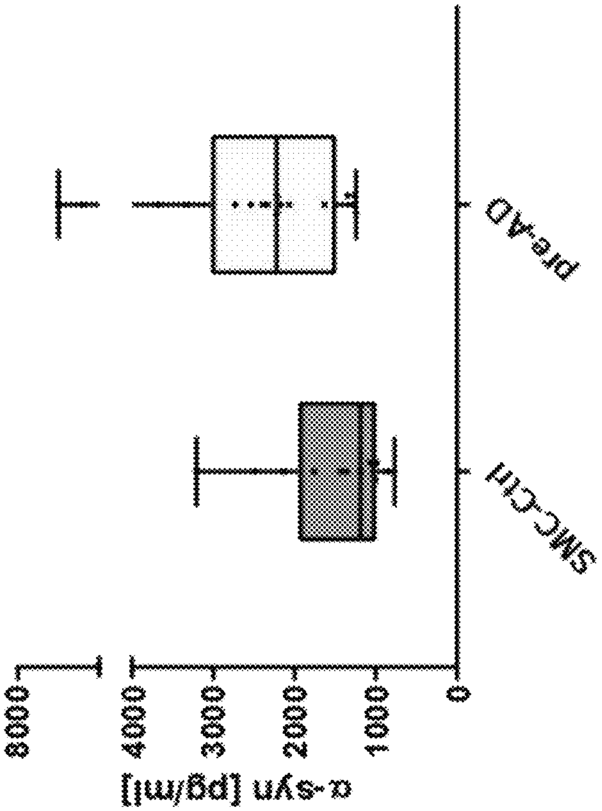
Figure 6H:
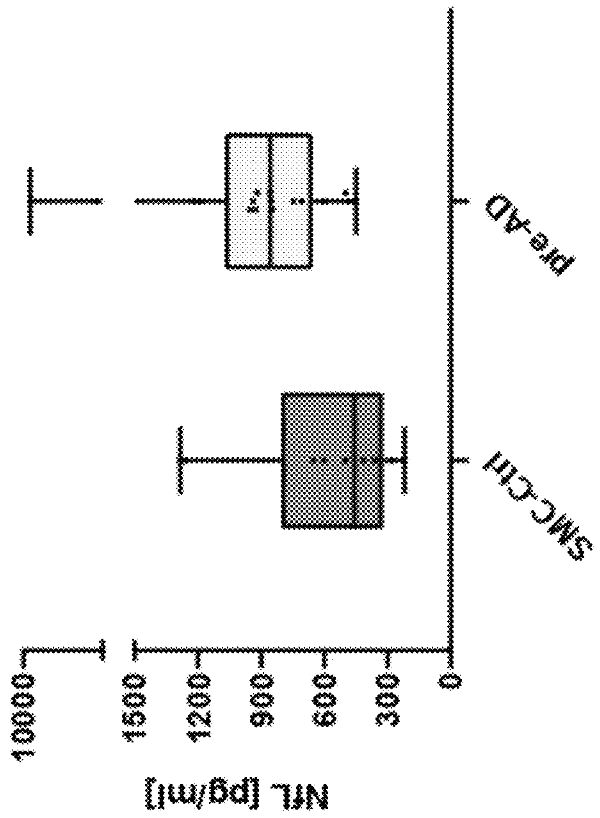
Figure 6G:
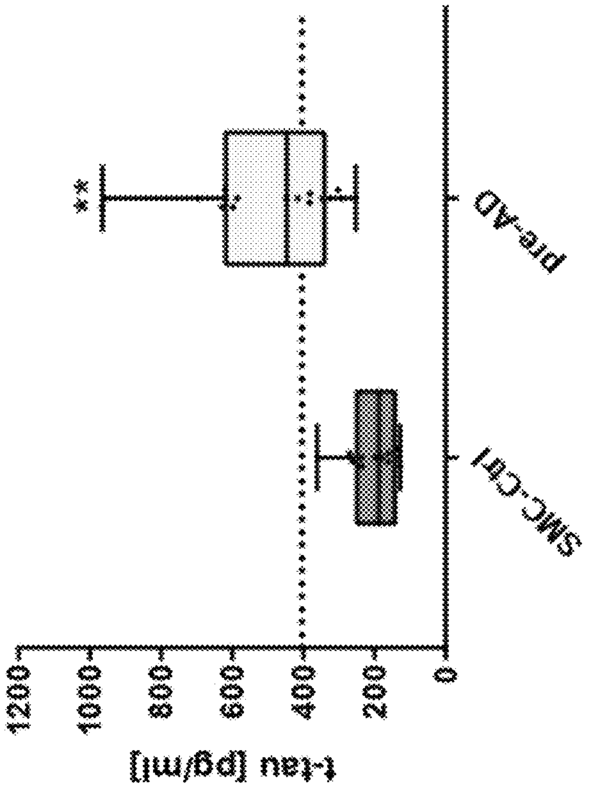
Figure 6J:
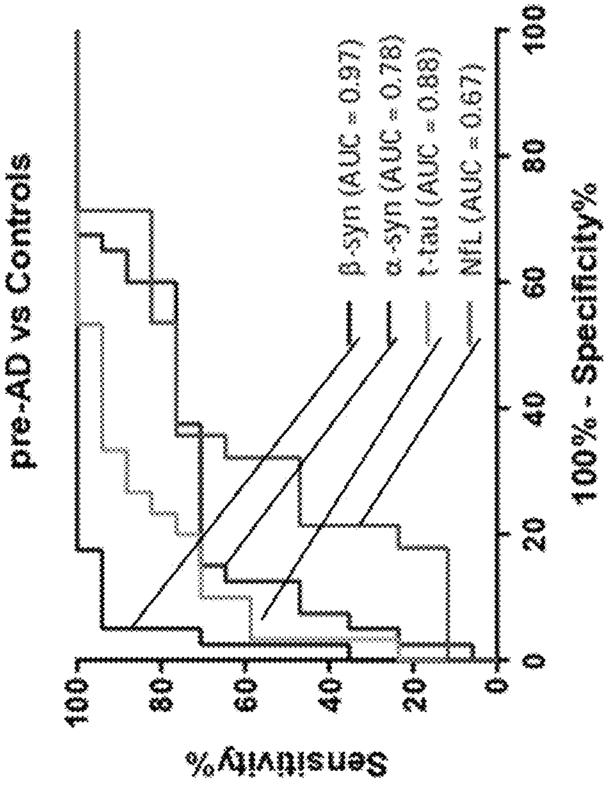
Figure 6I:
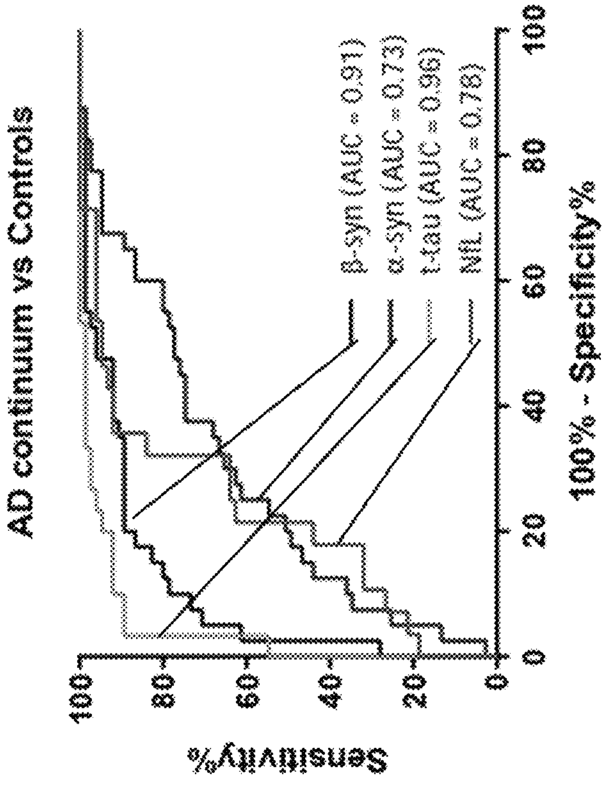
Figure 6K:
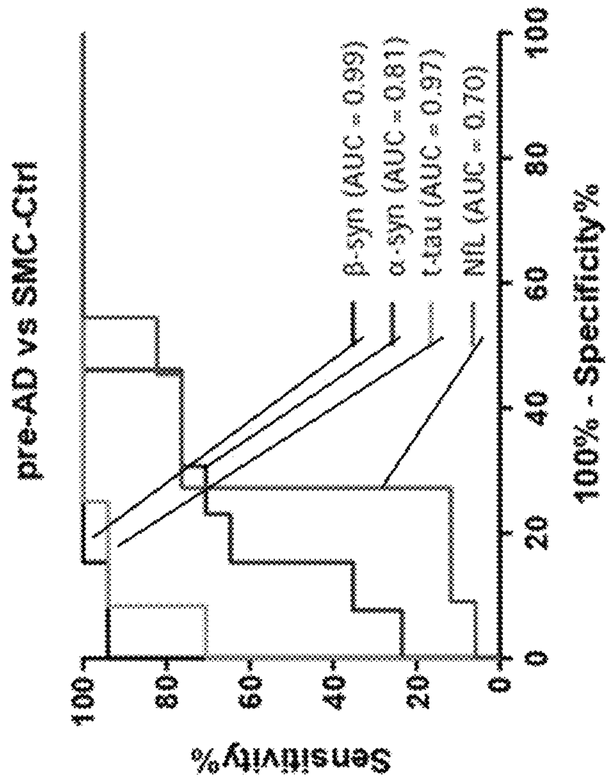
Figure 6L:
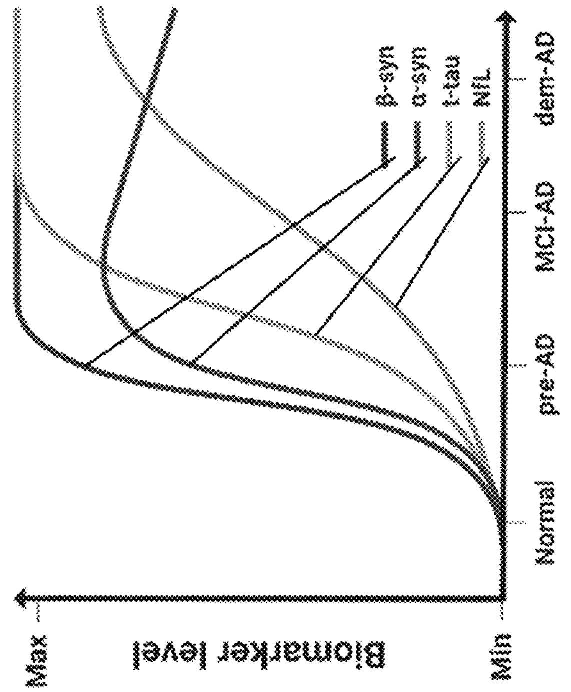
Figure 7B:
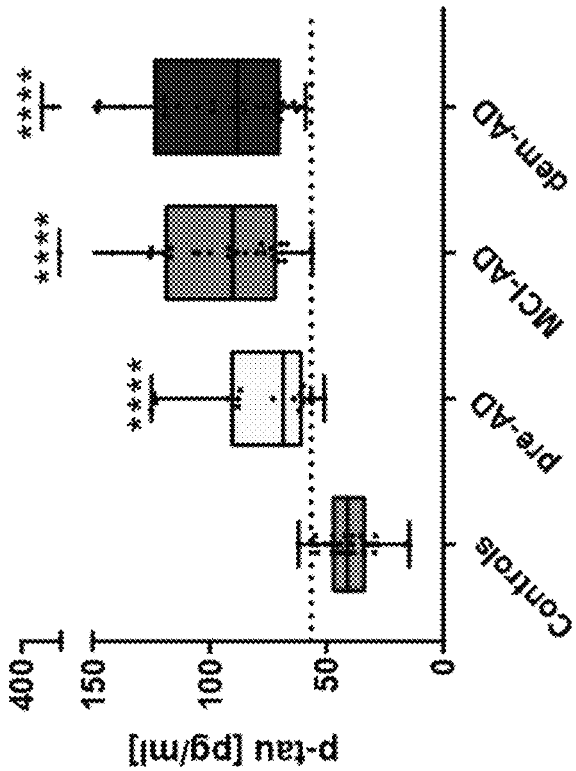
FIG. 7A to 7F illustrate cerebrospinal fluid AD core biomarker levels in AD continuum. Top panels show the comparison of FIG. 7A: Aβ42/40 (cut-off: 0.069)
Figure 7A:
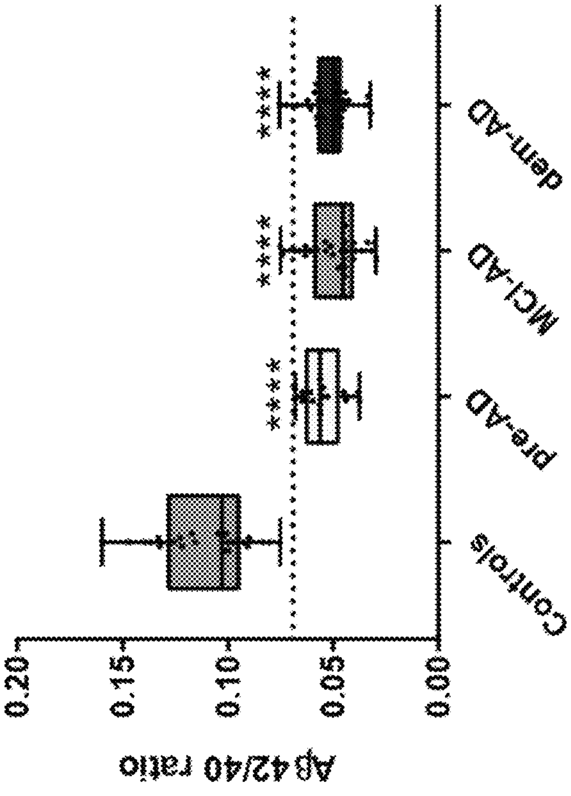
Figure 7C:
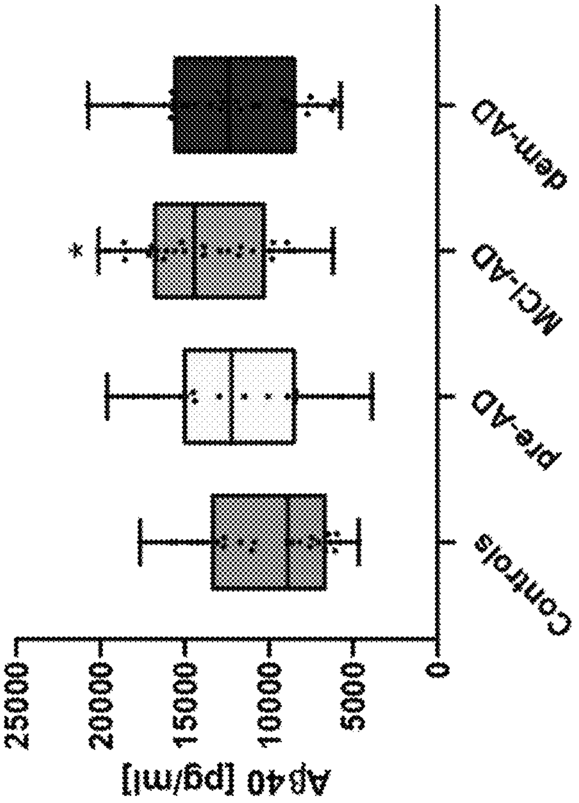
Figure 7D:
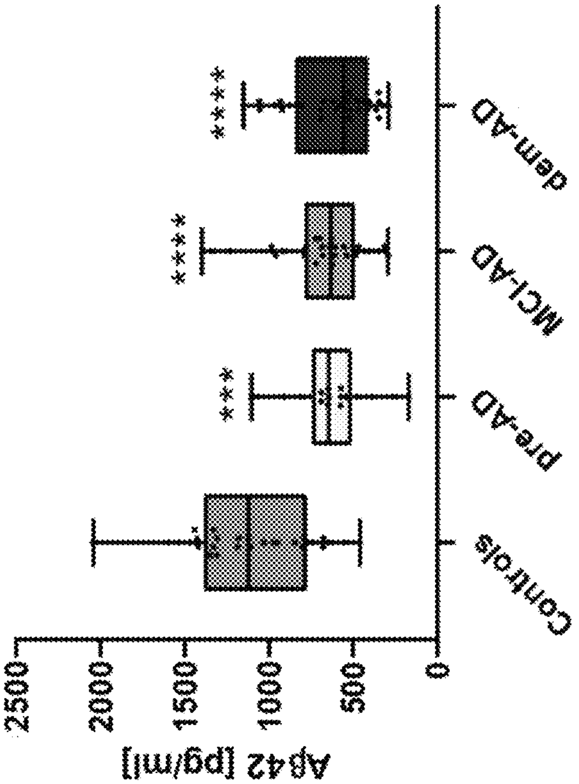
Figure 7E:
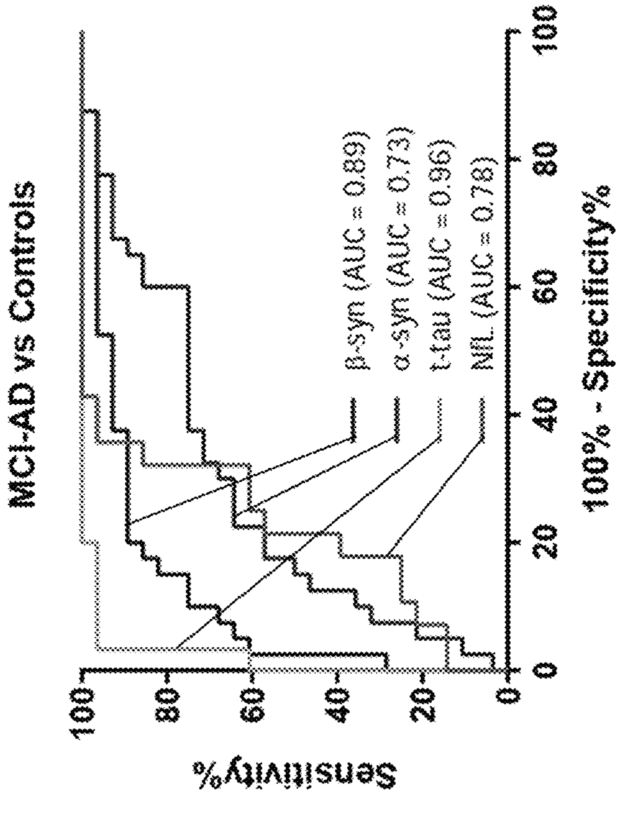
Figure 7F:
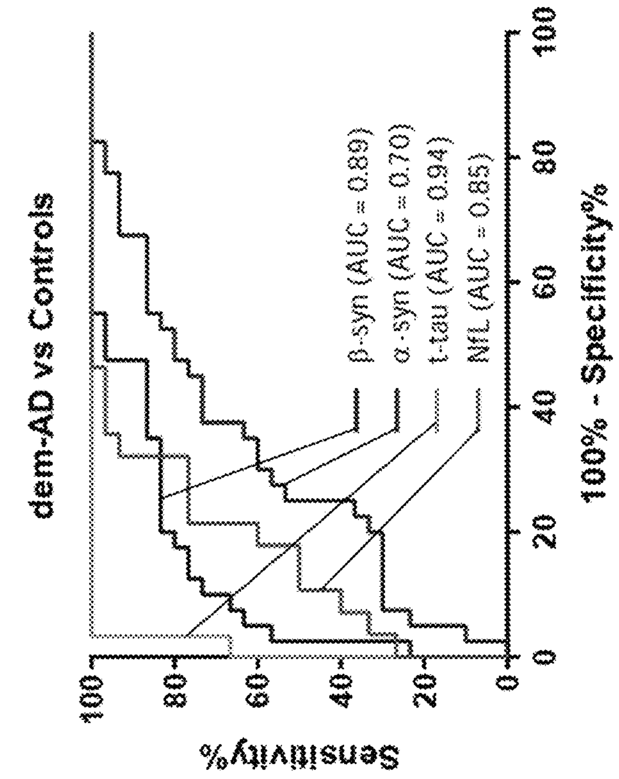

Noteworthy, both t-tau and NfL levels displayed normal values in most pre-AD cases and a progressive increase in MCI- and dem-AD stages, highlighting the association between ongoing neurodegeneration and clinical progression (19). The hypothetical distinct trajectories of synaptic and neuro-axonal biomarkers along the AD continuum suggest that synaptic derangement may be one of the very first events occurring in AD and may precede neurodegeneration (5) (FIG. 6L). Furthermore, the stronger correlation of β-syn with t-tau than with NfL may reflect distinct pathways of neurodegeneration, especially in the earliest disease phases (20).

In comparison to other candidate biomarkers of synaptic damage under investigation in AD, which also seem to be more correlated to disease progression and development of cognitive symptoms (21,22), β-syn seems to be steadily elevated along the whole AD continuum. Given the lack of knowledge about β-syn pathophysiology, one cannot exclude that β-syn may also participate to other pathological processes occurring in AD, such as neuroinflammation and protein misfolding. Nevertheless, the release of β-syn from degenerating synaptic terminals appears, to date, the most convincing explanation for the increased CSF values observed in AD as well as in prion disease patients (8,23).

In conclusion, CSF β-syn represents a promising biomarker for AD-related synaptic dysfunction at all disease stages, even in the preclinical phase and when t-tau and NfL levels are not yet significantly elevated. Further studies are required to fully elucidate and replicate these results.

References of Study 2

(1) Masters C L, Bateman R, Blennow K, Rowe C C, Sperling R A, Cummings J L. Alzheimer's disease. Nat Rev Dis Primers. 2015 Oct. 15; 1:15056.
(2) Jack C R, Bennett D A, Blennow K, Carrillo M C, Dunn B, Haeberlein S B, et al. NIA-AA Research Framework: Toward a biological definition of Alzheimer's disease. Alzheimers Dement. 2018 April; 14(4):535-62.
(3) Sperling R A, Aisen P S, Beckett L A, Bennett D A, Craft S, Fagan A M, et al. Toward defining the preclinical stages of Alzheimer's disease: recommendations from the National Institute on Aging-Alzheimer's Association workgroups on diagnostic guidelines for Alzheimer's disease. Alzheimers Dement. 2011 May; 7(3):280-92.
(4) Hampel H, Cummings J, Blennow K, Gao P, Jack C R, Vergallo A. Developing the ATX(N) classification for use across the Alzheimer disease continuum. Nat Rev Neurol. 2021 September; 17(9):580-9.
(5) Scheff S W, Price D A, Schmitt F A, Mufson E J. Hippocampal synaptic loss in early Alzheimer's disease and mild cognitive impairment. Neurobiol Aging. 2006 October; 27(10):1372-84.
(6) Oeckl P, Metzger F, Nagl M, von Arnim C A F, Halbgebauer S, Steinacker P, et al. Alpha-, Beta-, and Gamma-synuclein Quantification in Cerebrospinal Fluid by Multiple Reaction Monitoring Reveals Increased Concentrations in Alzheimer's and Creutzfeldt-Jakob Disease but No Alteration in Synucleinopathies. Mol Cell Proteomics. 2016; 15(10):3126-38.
(7) Oeckl P, Halbgebauer S, Anderl-Straub S, von Arnim C A F, Diehl-Schmid J, Froelich L, et al. Targeted Mass Spectrometry Suggests Beta-Synuclein as Synaptic Blood Marker in Alzheimer's Disease. J Proteome Res. 2020 Mar. 6; 19(3):1310-8.
(8) Halbgebauer S, Oeckl P, Steinacker P, Yilmazer-Hanke D, Anderl-Straub S, von Arnim C, et al. Beta-synuclein in cerebrospinal fluid as an early diagnostic marker of Alzheimer's disease. J Neurol Neurosurg Psychiatry. 2021 April; 92(4):349-56.
(9) Barba L, Paolini Paoletti F, Bellomo G, Gaetani L, Halbgebauer S, Oeckl P, et al. Alpha and Beta Synucleins: From Pathophysiology to Clinical Application as Biomarkers. Mov Disord. 2022 April; 37(4):669-83.
(10) Twohig D, Nielsen H M. α-synuclein in the pathophysiology of Alzheimer's disease. Mol Neurodegener. 2019 Jun. 11; 14:23.
(11) Milà-Alomà M, Salvadó G, Gispert J D, Vilor-Tejedor N, Grau-Rivera O, Sala-Vila A, et al. Amyloid beta, tau, synaptic, neurodegeneration, and glial biomarkers in the preclinical stage of the Alzheimer's continuum. Alzheimers Dement. 2020 October; 16(10):1358-71.

(12) McKhann G M, Knopman D S, Chertkow H, Hyman B T, Jack C R, Kawas C H, et al. The diagnosis of dementia due to Alzheimer's disease: recommendations from the National Institute on Aging-Alzheimer's Association workgroups on diagnostic guidelines for Alzheimer's disease. Alzheimers Dement. 2011 May; 7(3):263-9.

(13) Albert M S, DeKosky S T, Dickson D, Dubois B, Feldman H H, Fox N C, et al. The diagnosis of mild cognitive impairment due to Alzheimer's disease: recommendations from the National Institute on Aging-Alzheimer's Association workgroups on diagnostic guidelines for Alzheimer's disease. Alzheimers Dement. 2011 May; 7(3):270-9.

(14) Storandt M, Grant E A, Miller J P, Morris J C. Longitudinal course and neuropathologic outcomes in original vs revised MCI and in pre-MCI. Neurology. 2006 Aug. 8; 67(3):467-73.

(15) Teunissen C E, Petzold A, Bennett J L, Berven F S, Brundin L, Comabella M, et al. A consensus protocol for the standardization of cerebrospinal fluid collection and biobanking. Neurology. 2009 Dec. 1; 73(22):1914-22.

(16) Bellomo G, Paolini Paoletti F, Chipi E, Petricciuolo M, Simoni S, Tambasco N, et al. A/T/(N) Profile in Cerebrospinal Fluid of Parkinson's Disease with/without Cognitive Impairment and Dementia with Lewy Bodies. Diagnostics. 2020 Nov. 26; 10(12):1015.

(17) Halbgebauer S, Steinacker P, Verde F, Weishaupt J, Oeckl P, von Arnim C, et al. Comparison of CSF and serum neurofilament light and heavy chain as differential diagnostic biomarkers for ALS. J Neurol Neurosurg Psychiatry. 2022 January; 93(1):68-74.

(18) Parnetti L, Gaetani L, Eusebi P, Paciotti S, Hansson O, El-Agnaf O, et al. CSF and blood biomarkers for Parkinson's disease. Lancet Neurol. 2019; 18(6):573-86.

(19) Gaetani L, Blennow K, Calabresi P, Di Filippo M, Parnetti L, Zetterberg H. Neurofilament light chain as a biomarker in neurological disorders. J Neurol Neurosurg Psychiatry. 2019 August; 90(8):870-81.

(20) Abu-Rumeileh S, Capellari S, Stanzani-Maserati M, Polischi B, Martinelli P, Caroppo P, et al. The CSF neurofilament light signature in rapidly progressive neurodegenerative dementias. Alzheimers Res Ther. 2018 Jan. 11; 10(1):3.

(21) Camporesi E, Nilsson J, Brinkmalm A, Becker B, Ashton N J, Blennow K, et al. Fluid Biomarkers for Synaptic Dysfunction and Loss. Biomark� Insights. 2020 January; 15:117727192095031.

(22) Tarawneh R, D'Angelo G, Crimmins D, Herries E, Griest T, Fagan A M, et al. Diagnostic and Prognostic Utility of the Synaptic Marker Neurogranin in Alzheimer Disease. JAMA Neurol. 2016 May 1; 73(5):561-71.

(23) Halbgebauer S, Abu-Rumeileh S, Oeckl P, Steinacker P, Roselli F, Wiesner D, et al. Blood β-Synuclein and Neurofilament Light Chain During the Course of Prion Disease. Neurology. 2022 Feb. 2; 10.1212/WNL.0000000000200002.

(24) Delaby C, Teunissen C E, Blennow K, Alcolea D, Arisi I, Amar E B, et al. Clinical reporting following the quantification of cerebrospinal fluid biomarkers in Alzheimer's disease: An international overview. Alzheimers Dement. 2021 Dec. 22;

Supplement to Study 2

No difference in any biomarker levels could be found between male and female subjects, except for higher t-tau levels in female versus male control subjects ($p=0.02$) and lower NfL concentrations in female versus male AD cases ($p=0.005$). An older age and a higher percentage of females was disclosed in AD patients compared to controls ($p<0.0001$ and $p=0.005$, respectively) as well as in pre-AD cases compared to SMC-Ctrl subjects ($p=0.03$ and $p=0.004$, respectively).

CSF levels of Aβ42 were significantly decreased in pre-AD ($p=0.001$), MCI-AD ($p<0.0001$) and dem-AD cases ($p<0.0001$) compared to controls, while only MCI-AD had higher Aβ40 levels than controls ($p=0.02$) (FIG. 7A to 7F). CSF β-syn showed a weak but significant correlation with age in AD patients ($p=0.02$, $r=0.28$) but neither in controls nor in the pre-AD subgroup (Table S1).

In multiple logistic regression models including β-syn+ age and/or sex, β-syn remained an independent predictor of AD/pre-AD diagnosis, while both age and sex became non-significant in models with β-syn (Table S3). Moreover, no variable remained statistically significant in combined models for the comparison pre-AD versus SMC-Ctrl, probably due to the small sample size of diagnostic groups. Finally, the AUC values of regression models including β-syn alone, 3-syn+age, β-syn+sex and β-syn+age+sex were compared by means of DeLong test. AUCs of the models including β-syn+age and/or sex did not significantly differ from those including β-syn alone (Table S3).

TABLE S1

Correlation matrices between biomarker levels in the study cohort.

| | β-syn | α-syn | t-tau | NfL | Aβ40 | Aβ42 | Aβ42/40 | p-tau | Age |
|---|---|---|---|---|---|---|---|---|---|
| | Controls | | | | | | | | |
| β-syn | — | r = 0.48<br>p = 0.004 | r = 0.66<br>p = 0.0001 | — | r = 0.49<br>p = 0.01 | r = 0.39<br>p = 0.03 | — | — | — |
| α-syn | r = 0.48 | — | r = 0.69<br>p < 0.0001 | — | — | r = 0.41<br>p = 0.03 | — | r = 0.64<br>p = 0.0002 | r = 0.43<br>p = 0.01 |
| t-tau | r = 0.66<br>p = 0.0001 | r = 0.69<br>p < 0.0001 | — | — | r = 0.63<br>p = 0.001 | r = 0.61<br>p = 0.0006 | — | r = 0.78<br>p < 0.0001 | r = 0.48<br>p = 0.046 |
| NfL | — | — | — | — | — | — | — | — | r = 0.38<br>p = 0.045 |
| | AD continuum | | | | | | | | |
| β-syn | — | r = 0.69<br>p < 0.0001 | r = 0.40<br>p = 0.0004 | r = 0.32<br>p = 0.005 | r = 0.51<br>p < 0.0001 | r = 0.42<br>p = 0.0002 | — | r = 0.28<br>p = 0.02 | r = 0.28<br>p = 0.02 |
| α-syn | r = 0.69<br>p < 0.0001 | — | r = 0.39<br>p = 0.0005 | r = 0.24<br>p = 0.04 | r = 0.63<br>p < 0.0001 | r = 0.53<br>p < 0.0001 | — | r = 0.35<br>p = 0.002 | r = 0.29<br>p = 0.01 |

TABLE S1-continued

Correlation matrices between biomarker levels in the study cohort.

| | β-syn | α-syn | t-tau | NfL | Aβ40 | Aβ42 | Aβ42/40 | p-tau | Age |
|---|---|---|---|---|---|---|---|---|---|
| t-tau | r = 0.40<br>p = 0.0004 | r = 0.39<br>p = 0.0005 | — | r = 0.48<br>p < 0.0001 | r = 0.39<br>p = 0.0007 | — | — | r = 0.86<br>p < 0.0001 | - |
| NfL | r = 0.32<br>p = 0.0q5 | r = 0.24<br>p = 0.04 | r = 0.48<br>p < 0.0001 | — | — | — | — | r = 0.41<br>p = 0.0003 | r = 0.31<br>p = 0.006 |
| | pre-AD | | | | | | | | |
| β-syn | — | — | r = 0.88<br>p < 0.0001 | r = 0.59<br>p = 0.01 | r = 0.56<br>p = 0.03 | — | — | r = 0.84<br>p = 0.0001 | — |
| α-syn | — | — | — | — | — | — | — | — | — |
| t-tau | r = 0.88<br>p < 0.0001 | — | — | r = 0.71<br>p = 0.002 | r = 0.55<br>p = 0.03 | — | — | r = 0.87<br>p < 0.0001 | — |
| NfL | r = 0.59<br>p = 0.01 | — | r = 0.71<br>p = 0.002 | — | — | — | — | r = 0.69<br>p = 0.004 | — |
| | MCI-AD | | | | | | | | |
| β-syn | — | r = 0.81<br>p < 0.0001 | r = 0.41<br>p = 0.03 | — | r = 0.74<br>p < 0.0001 | r = 0.70<br>p < 0.0001 | — | — | — |
| α-syn | r = 0.81<br>p < 0.0001 | — | r = 0.46<br>p = 0.01 | r = 0.40<br>p = 0.03 | r = 0.81<br>p < 0.0001 | r = 0.65<br>p = 0.0002 | — | r = 0.42<br>p = 0.03 | — |
| t-tau | r = 0.41<br>p = 0.03 | r = 0.46<br>p = 0.01 | — | — | — | — | — | r = 0.85<br>p < 0.0001 | — |
| NfL | — | r = 0.40<br>p = 0.03 | — | — | — | r = 0.37<br>p = 0.05 | — | — | — |
| | dem-AD | | | | | | | | |
| β-syn | — | r = 0.78<br>p < 0.0001 | r = 0.40<br>p = 0.03 | r = 0.38<br>p = 0.04 | — | — | — | — | r = 0.57<br>p = 0.001 |
| α-syn | r = 0.78<br>p < 0.0001 | — | r = 0.62<br>p = 0.0003 | — | r = 0.64<br>p = 0.0002 | r = 0.44<br>p = 0.01 | — | r = 0.52<br>p = 0.003 | r = 0.52<br>p = 0.003 |
| t-tau | r = 0.40<br>p = 0.03 | r = 0.62<br>p = 0.0003 | — | — | r = 0.39<br>p = 0.03 | — | — | r = 0.85<br>p < 0.0001 | — |
| NfL | r = 0.38<br>p = 0.04 | — | — | — | — | — | — | — | r = 0.49<br>p = 0.005 |

Data are presented as p-value and Spearman r value only when statistically significant.

Abbreviations. Aβ40; amyloid-$\beta_{1-40}$ peptide; Aβ42: amyloid-$\beta_{1-42}$ peptide; AD: Alzheimer's disease; α-syn: α-synuelcin; β-syn: β-synuclein; dem-AD: Alzheimer's disease with dementia; MCI-AD: Alzheimer's disease with mild cognitive impairment; NfL: neurofilament light chain protein; pre-AD: preclinical Alzheimer's disease; p-tau: phosphorylated tau protein; t-tau: total tau protein.

TABLE S2

Diagnostic performance of cerebrospinal fluid biomarkers for AD.

| | AUC | Best cut-off | Sensitivity % | Specificity % | PLR |
|---|---|---|---|---|---|
| | | AD continuum vs Controls | | | |
| β-syn | 0.91 (0.85 to 0.96) | 313 | 86.7 (76.8 to 93.4) | 82.5 (67.2 to 92.7) | 5.0 |
| α-syn | 0.73 (0.63 to 0.82) | 1560 | 74.7 (63.3 to 84.0) | 62.5 (45.8 to 77.3) | 2.0 |
| t-tau | 0.96 (0.93 to 1.00) | 404 | 89.3 (80.1 to 95.3) | 96.7 (82.8 to 99.9) | 26.8 |
| NfL | 0.78 (0.67 to 0.90) | 665 | 92.0 (83.6 to 96.3) | 64.3 (45.8 to 79.3) | 2.1 |
| | | dem-AD vs Controls | | | |
| β-syn | 0.89 (0.81 to 0.96) | 319 | 80.0 (61.4 to 92.3) | 82.5 (67.2 to 92.7) | 4.6 |
| α-syn | 0.70 (0.57 to 0.82) | 1560 | 73.3 (54.1 to 87.7) | 62.5 (45.8 to 77.3) | 2.0 |
| t-tau | 0.99 (0.88 to 0.99) | 418 | 100.0 (88.4 to 100.0) | 96.7 (82.8 to 99.9) | 28.9 |
| NfL | 0.85 (0.75 to 0.95) | 776 | 93.3 (78.7 to 98.8) | 67.9 (49.3 to 82.1) | 2.9 |
| | | MCI-AD vs Controls | | | |
| β-syn | 0.89 (0.81 to 0.98) | 313 | 85.7 (67.3 to 96.0) | 82.5 (67.2 to 92.7) | 4.9 |
| α-syn | 0.73 (0.60 to 0.85) | 1917 | 64.3 (44.1 to 81.4) | 77.8 (61.5 to 89.2) | 2.9 |
| t-tau | 0.98 (0.92 to 1.00) | 405 | 96.4 (81.7 to 99.9) | 96.7 (82.8 to 99.9) | 28.9 |
| NfL | 0.78 (0.66 to 0.91) | 665 | 96.4 (82.3 to 99.8) | 64.3 (45.8 to 79.3) | 2.7 |
| | | pre-AD vs Controls | | | |
| β-syn | 0.97 (0.94 to 1.00) | 447 | 94.1 (71.3 to 99.9) | 95.0 (83.1 to 99.4) | 18.8 |
| α-syn | 0.78 (0.64 to 0.91) | 2066 | 70.6 (44.0 to 89.7) | 85.0 (70.2 to 94.3) | 4.7 |
| t-tau | 0.88 (0.79 to 0.98) | 303 | 88.2 (63.6 to 98.5) | 73.3 (54.1 to 88.7) | 3.3 |
| NfL | 0.67 (0.51 to 0.83) | 686 | 76.5 (52.7 to 90.4) | 64.3 (45.8 to 79.3) | 2.1 |

TABLE S2-continued

| Diagnostic performance of cerebrospinal fluid biomarkers for AD. | | | | | |
|---|---|---|---|---|---|
| | AUC | Best cut-off | Sensitivity % | Specificity % | PLR |
| pre-AD vs SMC-Ctrl | | | | | |
| β-syn | 0.99 (0.97 to 1.00) | 447 | 94.1 (71.3 to 99.9) | 100.0 (75.3 to 100.0) | — |
| α-syn | 0.81 (0.64 to 0.97) | 2154 | 64.7 (38.3 to 85.8) | 84.6 (54.5 to 98.1) | 4.2 |
| t-tau | 0.97 (0.91 to 1.00) | 281 | 94.1 (71.3 to 99.9) | 91.7 (61.5 to 99.8) | 11.3 |
| NfL | 0.70 (0.46 to 0.93) | 681 | 76.5 (52.7 to 90.4) | 72.7 (43.4 to 90.3) | 2.8 |

Best cut-offs were calculated by maximizing the Youden's index. AUC, sensitivity and specificity are reported with 95% confidence intervals in brackets.

Abbreviations. AD: Alzheimer's disease; α-syn: α-synuclein; AUC: area under the curve; β-syn: β-synuclein; dem-AD: Alzheimer's disease with dementia; MCI-AD: Alzheimer's disease with mild cognitive impairment; NfL: neurofilament light chain protein; PLR: positive likelihood ratio; pre-AD: preclinical Alzheimer's disease; SMC-Ctrl: control subjects with subjective memory complaints; t-tau: total tau protein.

TABLE S3

| Logistic regression models. | | | | | |
|---|---|---|---|---|---|
| Dependent variables | Predictors | β (95% CI) | Standard error | p-value | AUC (95% CI) |
| AD vs. controls | β-syn | 1.011 (1.007 to 1.017) | 0.002 | <0.0001 | 0.91 (0.85 to 0.96) |
| | age | 1.153 (1.085 to 1.236) | 0.033 | <0.0001 | 0.76 (0.66 to 0.86) |
| | sex | 3.188 (1.402 to 7.467) | 0.425 | 0.006 | 0.64 (0.53 to 0.75) |
| | β-syn | 1.010 (1.006 to 1.016) | 0.003 | <0.0001 | 0.92 (0.88 to 0.98) |
| | age | 1.080 (0.9998 to 1.175) | 0.041 | ns | p = 0.219* |
| | β-syn | 1.011 (1.007 to 1.017) | 0.003 | <0.0001 | 0.91 (0.87 to 0.97) |
| | sex | 1.145 (0.3402 to 3.707) | 0.603 | ns | p = 0.787* |
| | β-syn | 1.010 (1.006 to 1.016) | 0.003 | <0.0001 | 0.92 (0.88 to 0.98) |
| | age | 1.082 (0.998 to 1.172) | 0.041 | ns | p = 0.314* |
| | sex | 1.268 (0.362 to 4.364) | 0.628 | ns | |
| pre-AD vs. controls | β-syn | 1.017 (1.009 to 1.031) | 0.005 | 0.0008 | 0.97 (0.94 to 1.00) |
| | age | 1.144 (1.051 to 1.275) | 0.049 | 0.0054 | 0.75 (0.62 to 0.88) |
| | sex | 4.875 (1.405 to 20.21) | 0.668 | 0.0177 | 0.68 (0.53 to 0.84) |
| | β-syn | 1.022 (1.010 to 1.044) | 0.008 | 0.006 | 0.98 (0.95 to 1.00) |
| | age | 0.907 (0.704 to 1.089) | 0.102 | ns | p = 0.480* |
| | β-syn | 1.017 (1.009 to 1.032) | 0.005 | 0.0013 | 0.98 (0.94 to 1.00) |
| | sex | 3.744 (0.212 to 148.5) | 1.540 | ns | p = 0.379* |
| | β-syn | 1.020 (1.010 to 1.043) | 0.008 | 0.0074 | 0.98 (0.95 to 1.00) |
| | age | 0.926 (0.713 to 1.127) | 0.108 | ns | p > 0.999* |
| | sex | 2.511 (0.075 to 115.3) | 1.700 | ns | |
| pre-AD vs. SMC-Ctrl | β-syn | 1.021 (1.009 to 1.048) | 0.009 | 0.018 | 0.99 (0.97 to 1.00) |
| | age | 1.145 (1.030 to 1.315) | 0.061 | 0.0253 | 0.73 (0.54 to 0.92) |
| | sex | 10.83 (2.178 to 70.71) | 0.872 | 0.0063 | 0.76 (0.58 to 0.94) |
| | β-syn | 1.044 (1.013 to 1.159) | 0.027 | ns | 0.99 (0.98 to 1.00) |
| | age | 0.070 (0.304 to 1.050) | 0.269 | ns | p = 0.480* |
| | β-syn | 1.055 (1.013 to 1.648) | 0.057 | ns | 0.99 (0.98 to 1.00) |
| | sex | 5.864 (0.452 to 78.5) | 2.951 | ns | p = 0.480* |
| | β-syn | 1.015 (1.006 to 1.024) | 0.030 | ns | 1.00 (0.84 to 1.00) |
| | age | 0.879 (0.374 to 1.165) | 0.279 | ns | p = 0.408* |
| | sex | 4.256 (0.048 to 86.4) | 1.820 | ns | |

Results of multivariate logistic regression analysis in the comparisons between AD versus controls, pre-AD versus controls and pre-AD versus SMC-Ctrl. AD/pre-AD diagnosis and sex are considered as categorical dependent (diagnosis=1) and independent (female gender=1) variables. β-values and area under the curve values (AUCs) are reported with 95% confidence intervals (95% CI) in parenthesis. *p-values refer to the DeLong test for the comparison of each AUC value with the models including β-syn alone. Abbreviations. AD: Alzheimer's disease; β-syn: β-synuclein; pre-AD: preclinical Alzheimer's disease; SMC-Ctrl: controls with subjective memory complaints.

Many variations and modifications may be made to the preferred embodiments of the invention without departing substantially from the spirit and principles of the invention. All such modifications and variations are intended to be included herein within the scope of the present invention, as defined by the following claims.

We claim:

1. An assay kit for determining a concentration of beta-synuclein in a cerebrospinal fluid (CSF) sample taken from a patient, for use in an ex vivo method of diagnosing a disease associated with synaptic degeneration, the method comprising obtaining a cerebrospinal fluid (CSF) sample taken from a patient, and determining a concentration of beta-synuclein in the cerebrospinal fluid (CSF), the assay kit comprising a sandwich enzyme-linked immunosorbent assay (ELISA) for determining the concentration of beta-synuclein in the cerebrospinal fluid (CSF) sample, wherein the sandwich ELISA includes capture and detection antibodies against beta-synuclein, and wherein the capture and detection antibodies include a monoclonal capture antibody against beta- and alpha-synuclein and a detection antibody specific for beta-synuclein.

2. The assay kit of claim 1, wherein the detection antibody is a biotinylated antibody.

3. The assay kit of claim 1, further comprising a plurality of beta-synuclein calibrators prepared from recombinant beta-synuclein and blocking buffer, each of the calibrators of the plurality of the beta-synuclein calibrators comprising recombinant beta-synuclein and blocking buffer, and the beta-synuclein concentrations of the plurality of the beta-synuclein calibrators ranging from 10 pg/ml to at least 1,000 pg/ml.

* * * * *